(12) United States Patent
Li et al.

(10) Patent No.: US 8,591,877 B2
(45) Date of Patent: Nov. 26, 2013

(54) CELLULOSE-BASED NANOPARTICLES FOR DRUG DELIVERY

(75) Inventors: Shyh-Dar Li, Toronto (CA); Mark John Ernsting, Toronto (CA); Wei-Lun Tang, Toronto (CA)

(73) Assignee: Ontario Institute for Cancer Research, Toronto (CA)

( * ) Notice: Subject to any disclaimer, the term of this patent is extended or adjusted under 35 U.S.C. 154(b) by 5 days.

(21) Appl. No.: 13/363,822

(22) Filed: Feb. 1, 2012

(65) Prior Publication Data

US 2012/0219508 A1 Aug. 30, 2012

Related U.S. Application Data

(60) Provisional application No. 61/438,842, filed on Feb. 2, 2011.

(51) Int. Cl.
*A61K 31/74* (2006.01)

(52) U.S. Cl.
USPC .................................................. 424/78.17

(58) Field of Classification Search
None
See application file for complete search history.

(56) References Cited

U.S. PATENT DOCUMENTS

| | | | | |
|---|---|---|---|---|
| 4,520,192 | A | 5/1985 | Namikoshi | 536/66 |
| 5,792,856 | A | 8/1998 | Allen et al. | 536/66 |
| 6,063,396 | A * | 5/2000 | Kelleher | 424/428 |
| 2010/0151582 | A1 | 6/2010 | Fazioni et al. | 436/93 |

FOREIGN PATENT DOCUMENTS

EP 1614696 1/2006

OTHER PUBLICATIONS

Ahmed F, Pakunlu RI, Brannan A, Bates F, Minko T, Discher DE. "Biodegradable polymersomes loaded with both paclitaxel and doxorubicin permeate and shrink tumors, inducing apoptosis in proportion to accumulated drug". *J Control Release.* Nov. 28, 2006;116(2):150-8.

Andresen TL, Jensen SS, Jorgensen K. "Advanced strategies in liposomal cancer therapy: problems and prospects of active and tumor specific drug release". *Prog Lipid Res.* Jan. 2005;44(1):68-97.

Auzenne E, Ghosh SC, Khodadadian M, Rivera B, Farquhar D, Price RE, et al. "Hyaluronic acid-paclitaxel: antitumor efficacy against CD44(+) human ovarian carcinoma xenografts". *Neoplasia.* Jun. 2007;9(6):479-86.

Branca RT, Cleveland ZI, Fubara B, Kumar CS, Maronpot RR, Leuschner C, et al. "Molecular MRI for sensitive and specific detection of lung metastases". *Proc Natl Acad Sci U S A.* Feb. 23, 2010;107(8):3693-7.

Cera C, Palumbo M, Stefanelli S, Kassa M, Palu G. "Water-soluble polysaccharide-anthracycline conjugates: biological activity". *Anticancer Drug Des.* Apr. 1992;7(2): 143-51.

Charpentier D, Mocanu G, Carpov A, Chapelle S, Merle L, Muller G. "New hydrophobically modified carboxymethylcellulose derivitives". *Carbohydrate Polymers.* 1997;33:177-86.

de Smet M, Heijman E, Langereis S, Hijnen N, Grull H. "Magnetic resonance imaging of high intensity focused ultrasound mediated drug delivery from temperature sensitive liposomes; An in vivo proof-of-concept study". *J Control Release.* Nov. 5, 2010.

(Continued)

*Primary Examiner* — Paul Dickinson

(74) *Attorney, Agent, or Firm* — Fulbright & Jaworski, L.L.P.; Scott D. Rothenberger

(57) ABSTRACT

In one aspect, there is provided a compound comprising an acetylated carboxymethylcellulose (CMC-Ac) covalently linked to: at least one poly(ethylene glycol) (PEG), and at least one hydrophobic drug. In another aspect, a self-assembling nanoparticle composition comprising such compounds is provided.

36 Claims, 12 Drawing Sheets

(56) References Cited

OTHER PUBLICATIONS

De Souza R, Zahedi P, Mariyama E, H., Allen C, Wilson BC, Paquette-Miller M. "Continuous docetaxel chemotherapy improves therapeutic efficacy in murine models of ovarian cancer". *Molecular Cancer Therapeutics.* 2010;9(6):1820-30.
Dias MHM, Lauterbur PC. "Ferromagnetic particles as contrast agents for magnetic resonance imaging of liver and spleen". *Megnelic Resonance in Medicine.* 1986;3:328-30.
Discher DE, Ahmed F. "Polymersomes". *Annu Rev Biomed Eng.* 2006;8:323-41.
Drummond DC, Noble CO, Hayes ME, Park JW, Kirpotin DB. "Pharmacokinetics and in vivo drug release rates in liposomal nanocarrier development". *J Pharm Sci.* Nov. 2008;97(11):4696-740.
Dubey PK, Mishra V, Jain S, Mahor S, Vyas SP. "Liposomes modified with cyclic RGD peptide for tumor targeting". *J Drug Target.* Jun. 2004; I2(5):257-64.
Duncan R. "Polymer conjugates as anticancer nanomedicines". *Nat Rev Cancer.* Sep. 2006;6(9):688-701.
Duncan R., "Development of HPMA copolymer-anticancer conjugates: clinical experience and lessons learnt". *Adv Drug Deliv Rev.* Nov. 12, 2009;61(13):1131-48.
Duncan R., "The dawning era of polymer therapeutics", *Nat Rev Drug Discov.* May 2003; 2(5):347-60.
Ertel SI, Ratner BD, Kaul A, Schway MB, Horbett TA. "In vitro study of the intrinsic toxicity of synthetic surfaces to cells". *J Biomed Mater Res.* Jun. 1994;28(6):667-75.
Esmaeili F, Dinarvand R, Ghahremani MH, Amini M, Rouhani H, Sepehri N, et al. "Docetaxel-albumin conjugates: preparation, in vitro evaluation and biodistribution studies". *J Pharm Sci.* Aug. 2009;98(8):2718-30.
Etrych T, Sirova M, Starovoytova L, Rihova B, Ulbrich K. "HPMA copolymer conjugates of paclitaxel and docetaxel with pH-controlled drug release". *Mol Pharm.* Aug. 2, 2010;7(4):1015-26.
EU. Assessment Report: Docefrez. In: Agency EM, editor. London; 2010.
Fairley N, Hoang B, Allen C. "Morphological control of poly(ethylene glycol)-block-poly(epsilon-caprolactone) copolymer aggregates in aqueous solution". *Biomacromolecules.* Sep. 2008;9(9):2283-91.
FDA. *Database of Select Committee on GRAS Substances (SCOGS) Reviews.* 2010.
FDA. Home> Medical Devices> Products and Medical Procedures> Device Approvals and Clearances: OP-1 Putty—H020008. 2010.
FDA. Inactive Ingredients Database. Rockville; 2010.
Feng Z, Zhao G, Yu L, Gough D, Howell SB. "Preclinical efficacy studies of a novel nanoparticle-based formulation of paclitaxel that out-performs Abraxane". *Cancer Chemother Pharmacol.* Apr. 2010;65(5):923-30.
Gabizon A, Shmeeda H, Barenholz Y. "Pharmacokinetics of pegylated liposomal Doxorubicin: review of animal and human studies". *Clin Pharmacokinet.* 2003;42(5):419-36.
Gaucher G, Marchessault RH, Leroux JC. "Polyester-based micelles and nanoparticles for the parenteral delivery of taxanes". *J Control Release.* Apr. 2, 2010;143(1):2-12.
Gelderblom H, Verweij J, Nooter K, Sparreboom A. "Cremophor EL: The drawbacks and advantages of vehicle selection for drug formulation". *Eur. J Cancer.* Sep. 2001;37(13):1590-8.
Greish K., "Enhanced permeability and retention (EPR) effect for anticancer nanomedicine drug targeting". *Methods Mol Biol.* 2010;624:25-37.
Greish K., "Enhanced permeability and retention of macromolecular drugs in solid tumors: a royal gate for targeted anticancer nanomedicines". *J Drug Target.* Aug.-Sep. 2007;15(7-8):457-64.
Hamaguchi T, Kato K, Yasui H, Morizane C, Ikeda M, Ueno H, et al. "A phase 1 and pharmacokinetic study of NK105, a paclitaxel-incorporating micellar nanoparticle formulation". *Br J Cancer.* Jul. 16, 2007;97(2):170-6.
Hamaguchi T, Matsumura Y, Suzuki M, Shimizu K, Goda R, Nakamura I, et al. "NK105, a paclitaxel-incorporating micellar nanoparticle formulation, can extend in vivo antitumour activity and reduce the neurotoxicity of paclitaxel". *Br J Cancer.* Apr. 11, 2005;92(7):1240-6.
Harding FA, Stickler MM, Razo J, Dubridge RB. "The immunogenicity of humanized and fully human antibodies: residual immunogenicity resides in the CDR regions". *MAbs.* May 2010;2(3):256-65.
Harris JM, Martin NE, Modi M. "Pegylation: a novel process for modifying pharmacokinetics". *Clin Pharmacokinet.* 2001;40(7):539-51.
Harris JM, Zalipsky S, American Chemical Society. Division of Polymer Chemistry., American Chemical Society. Meeting. Polyethylene glycol) : chemistry and biological applications. Washington, DC: American Chemical Society; 1997.
Hashizume H, Baluk P, Morikawa S, McLean JW, Thurston G, Roberge S, et al., "Openings between defective endothelial cells explain tumor vessel leakiness". *Am J Pathol.* Apr. 2000;156(4):1363-80.
Hilkens PH, Verweij J, Vecht CJ, Stoter G, van den Bent MJ. "Clinical characteristics of severe peripheral neuropathy induced by docetaxel (Taxotere)". *Ann Oncol.* Feb. 1997;8(2): 187-90.
Hoang B, Lee H, Reilly R, Allen C. "Non-Invasive Monitoring of the Fate of 111 In-Labeled Block Copolymer Micelles by High Resolution and High Sensitivity MicroSPECT/CT Imaging". *Mol Pharm.* Feb. 2, 2009.
Hobbs SK, Monsky WL, Yuan F, Roberts WG, Griffith L, Torchilin VP, et al. "Regulation of transport pathways in tumor vessels: role of tumor type and microenvironment". *Proc Natl Acad Sci USA.* Apr. 14, 1998;95(8):4607-12.
Hou W, Watters JW, McLeod HL. "Simple and rapid docetaxel assay in plasma by protein precipitation and high-performance liquid chromatography-tandem mass spectrometry". *J Chromatogr B Analyt Technol Biomed Life Sci.* May 25, 2004;804(2):263-7.
Immordino ML, Dosio F, Cattel L. "Stealth liposomes: review of the basic science, rationale, and clinical applications, existing and potential". *Int J Nanomedicine.* 2006;l(3):297-315.
Inoue K, Kumazawa E, Kuga H, Susaki H, Masubuchi N, Kajimura T. "CM-dextran-polyalcohol-camptothecin conjugate: DE-310 with a novel carrier system and its preclinical data". *Adv Exp Med Biol.* 2003;519:145-53.
Janes KA, Calvo P, Alonso MI. "Polysaccharide colloidal particles as delivery systems for macromolecules". *Adv Drug Deliv Rev.* Mar. 23, 2001;47(1):83-97.
Jones S. "Head-to-head: Docetaxel challenges paclitaxel". *EJC Supplements.* 2006;4:4-8.
Kaida S, Cabral H, Kumagai M, Kishimura A, Terada Y, Sekino M, et al. "Visible drug delivery by supramolecular nanocarriers directing to single-platformed diagnosis and therapy of pancreatic tumor model". *Cancer Res.* Sep. 15, 2010;70(18):7031-41.
Kamat AA, Kim TJ, Landen CN, Jr., Lu C, Han LY, Lin YG, et al. "Metronomic chemotherapy enhances the efficacy of antivascular therapy in ovarian cancer". *Cancer Res.* Jan. 1, 2007;67(1):281-8.
Katz JS, Levine DH, Davis KP, Bates FS, Hammer DA, Burdick JA. "Membrane stabilization of biodegradable polymersomes". *Langmuir.* Apr. 21, 2009;25(8):4429-34.
Kerns EH, Volk KJ, Hill SE, Lee MS. "Profiling taxanes in Taxus extracts using lc/ms and lc/ms/ms techniques". *J Nat Prod.* Oct. 1994;57(10):1391-403.
Kerns EH, Volk KJ, Hill SE. "Profiling new taxanes using LC/MS and LC/MS/MS substructural analysis techniques". *Rapid Communications in Mass Spectrometry.* 1995;9:1539-45.
Kirpotin DB, Drummond DC, Shao Y, Shalaby MR, Hong K, Nielsen UB, et al. "Antibody targeting of long-circulating lipidic nanoparticles does not increase tumor localization but does increase internalization in animal models". *Cancer Res.* Jul. 1, 2006;66(13):6732-40.
Koning GA, Kamps JA, Scherphof GL. "Interference of macrophages with immunotargeting of liposomes". *J Liposome Res.* Feb.-May 2002;12(1-2):107-19.
Kumar D, Tomar RS, Deolia SK, Mitra M, Mukherjee R, Burman AC. "Isolation and characterization of degradation impurities in docetaxel drug substance and its formulation". J Pharm Biomed Anal. Mar. 12, 2007;43(4):1228-35.

(56) References Cited

OTHER PUBLICATIONS

Landais P, Meresse V, Ghislain JC. "Evaluation and validation of diagnostic tests for guiding therapeutic decisions". *Therapie.* May-Jun. 2009;64(3):187-201.

Lavasanifar A, Samuel J, Kwon GS. "Poly(ethylene oxide)-block-poly(L-amino acid) micelles for drug delivery". *Adv Drug Deliv Rev.* Feb. 21, 2002;54(2):169-90.

Le Garrec D, Gori S, Luo L, Lessard D, Smith DC, Yessine MA, et al. "Poly(N-vinylpyrrolidone)-block-poly(D,L-lactide) as a new polymeric solubilizer for hydrophobic anticancer drugs: in vitro and in vivo evaluation". *J Control Release.* Sep. 14, 2004;99(1):83-101.

Letchford K, Liggins R, Wasan KM, Burt H. "In vitro human plasma distribution of nanoparticulate paclitaxel is dependent on the physicochemical properties of poly(ethylene glycol)-block-poly(caprolactone) nanoparticles". *Eur J Pharm Biopharm.* Feb. 2007;71(2):196-206.

Li C, Newman RS, Wu QP, Ke S, Chen W, Hutto T, et al. "Biodistribution of paclitaxel and poly(L-glutamic acid)-paclitaxel conjugate in mice with ovarian OCa-1 tumor". *Cancer Chemother Pharmacol.* 2000;46(5):416-22.

Li C, Price JE, Milas L, Hunter NR, Ke S, Yu DF, et al. "Antitumor activity of poly(L-glutamic acid)-paclitaxel on syngeneic and xenografted tumors". *Clin Cancer Res.* Apr. 1999;5(4):891-7.

Li C, Wallace S., "Polymer-drug conjugates: recent development in clinical oncology", *Adv Drug Deliv Rev.* May 22, 2008; 60(8):886-98.

Li C, Yu DF, Newman RA, Cabral F, Stephens LC, Hunter N, et al. "Complete regression of well-established tumors using a novel water-soluble poly(L-glutamic acid)-paclitaxel conjugate". *Cancer Res.* Jun. 1, 1998;58(11):2404-9.

Li SD, Huang L. "Pharmacokinetics and biodistribution of nanoparticles". *Mol Pharm.* Jul.-Aug. 2008;5(4):496-504.

Lim WT, Tan EH, Toh CK, Hee SW, Leong SS, Ang PC, et al. "Phase I pharmacokinetic study of a weekly liposomal paclitaxel formulation (Genexol-PM) in patients with solid tumors". *Ann Oncol.* Feb. 2010;21(2):382-8.

Lindner LH, Hossann M. "Factors affecting drug release from liposomes". *Curr Opin Drug Discov Devel.* Jan. 2010;13(1): 111-23.

Lipinski CA. "Drug-like properties and the causes of poor solubility and poor permeability". *J Pharmacol Toxicol Methods.* Jul.-Aug. 2000;44(1):235-49.

Liu B, Yang M, Li R, Ding Y, Qian X, Yu L, et al. "The antitumor effect of novel docetaxel-loaded thermosensitive micelles". *Eur J Pharm Biopharm.* Jun. 2008;69(2):527-34.

Liu J, Zahedi P, Zeng F, Allen C. "Nano-sized assemblies of a PEG-docetaxel conjugate as a formulation strategy for docetaxel". *J Pharm Sci.* Aug. 2008;97(8):3274-90.

Liu Z, Jiao Y, Wang Y, Zhou C, Zhang Z. "Polysaccharides-based nanoparticles as drug delivery systems". *Adv Drug Deliv Rev.* Dec. 14, 2008;60(15):1650-62.

Lord R, Nair S, Schache A, Spicer J, Somaihah N, Khoo V, et al. "Low dose metronomic oral cyclophosphamide for hormone resistant prostate cancer: a phase II study". *J Urol.* Jun. 2007;177(6):2136-40; discussion 40.

Mark J. Ernsting, Warren D. Foltz, Elijus Undzys, Tatsuaki Tagami, Shyh-Dar Li. "Tumor-targeted drug delivery using Mr-contrasted docetaxel Carboxymethylcellulose nanoparticles." *Biomaterials.* 2012;33:3931-3941.

Mark J. Ernsting, Wei-Lun Tang, Noah McCallum, Shyh-Dar Li. "Preclinical pharmacokinetic, biodistribution, and anti-cancer efficacy studies of a docetaxel-carboxymethylcellulose nanoparticle in mouse models". *Biomaterials.* 2012;33:1445-1454.

Mark J. Ernsting, Wei-Lun Tang, Noah McCallum, Shyh-Dar Li. "Synthetic Modification of Carboxymethylcellulose and Use Thereof to Prepare a Nanoparticle Forming Conjugate of Docetaxel for Enhanced Cytotoxicity against Cancer Cells". *Bioconjugate Chem.* 2011;22:2474-2486.

Matsumura Y, Maeda H., "A new concept for macromolecular therapeutics in cancer chemotherapy: mechanisms of tumoritropic accumulation of proteins and the antitumor agent smancs". *Cancer Research.* 1986;46:6387-92.

Misra R, Acharya S, Sahoo SK. "Cancer nanotechnology: application of nanotechnology in cancer therapy". *Drug Discov Today.* Oct. 2010;15(19-20):842-50.

Morais JM, Papadimitrakopoulos F, Burgess DJ. "Biomaterials/tissue interactions: possible solutions to overcome foreign body response". *AAPS J.* Jun. 2010;12(2):188-96.

Owens DE, 3rd, Peppas NA. "Opsonization, biodistribution, and pharmacokinetics of polymeric nanoparticles". *Int J Pharm.* Jan. 3, 2006;307(1):93-102.

Prabaharan M, Mano JF. "Chitosan-based particles as controlled drug delivery systems". *Drug Deliv.* Jan.-Feb. 2005;12(1):41-57.

Prabaharan M. "Review paper: chitosan derivatives as promising materials for controlled drug delivery". *J Biomater Appl.* Jul. 2008;23(1):5-36.

Ringsdorf H., "Structure and properties of pharmacologically active polymers", *Journal of Polymer Science, Polymer Symposia.* 1975;51:135-53.

Santerre JP, Woodhouse K, Laroche G, Labow RS. "Understanding the biodegradation of polyurethanes: from classical implants to tissue engineering materials". *Biomaterials.* Dec. 2005;26(35):7457-70.

Saravanakumar G, Min KH, Min DS, Kim AY, Lee CM, Cho YW, et al. "Hydrotropic oligomer-conjugated glycol chitosan as a carrier of paclitaxel: synthesis, characterization, and in vivo biodistribution". *J Control Release.* Dec. 16, 2009;140(3):210-7.

Sasaki A, Boyce BF, Story B, Wright KR, Chapman M, Boyce R, et al. "Bisphosphonate risedronate reduces metastatic human breast cancer burden in bone in nude mice". *Cancer Res.* Aug. 15, 1995;55(16):3551-7.

Seymour LW, Duncan R, Strohalm J, Kopecek J., "Effect of molecular weight (Mw) of N-(2-hydroxypropyl)methacrylamide copolymers on body distribution and rate of excretion after subcutaneous, intraperitoneal, and intravenous administration to rats". *J Biomed Mater Res.* Nov. 1987;21(11):1341-58.

Shelley WB, Talanin N, Shelley ED. "Polysorbate 80 hypersensitivity". *Lancet.* May 20, 1995;345(8960):1312-3.

Shishido T, Mieda H, Hwang SY, Nishimura Y, Tanaka T, Ogino C, et al. "Affibodydisplaying bionanocapsules for specific drug delivery to HER2-expressing cancer cells". *Bioorg Med Chem Lett.* Oct. 1, 2010;20(19):5726-31.

Singer JW, Shaffer B, Baker B, Bernareggi A, Stromatt S, Nienstedt D, et al. "Paclitaxel poliglumex (XYOTAX; CT-2103): an intracellularly targeted taxane". *Anticancer Drugs.* Mar. 2005;16(3):243-54.

Singla AK, Garg A, Aggarwal D. "Paclitaxel and its formulations". *Int J Pharm.* Mar. 20, 2002;235(I-2):179-92.

Soepenberg O, de Jonge MJ, Sparreboom A, de Bruin P, Eskens FA, de Heus G, et al. "Phase 1 and pharmacokinetic study of DE-310 in patients with advanced solid tumors". *Clin Cancer Res.* Jan. 15, 2005;11(2 Pt I):703-11.

Sugahara S, Kajiki M, Kuriyama H, Kobayashi TR. "Complete regression of xenografted human carcinomas by a paclitaxel-carboxymethyl dextran conjugate (AZ10992)". *J Control Release.* Jan. 22, 2007;117(1):40-50.

Sun S, Zeng H. "Size-controlled synthesis of magnetite nanoparticles". *J Am Chem Soc.* Jul. 17, 2002;124(28):8204-5.

Svenson S, Tomalia DA. "Dendrimers in biomedical applications--reflections on the field". *Adv Drug Deliv Rev.* Dec. 14, 2005;57(15):2106-29.

Tekade RK, Kumar PV, Jain NK. "Dendrimers in oncology: an expanding horizon". *Chem Rev.* Jan. 2009;109(1):49-87.

Tomalia DA, Reyna LA, Svenson S. "Dendrimers as multi-purpose nanodevices for oncology drug delivery and diagnostic imaging". *Biochem Soc Trans.* Feb. 2007;35(Pt I):61-7.

Uglea CV, Pary A, Corjan M, Dumitriu AD, Ottenbrite RM. "Biodistribution and antitumor activity induced by carboxymethylcellulose conjugates". *Journal of Bioactive and Compatible Polymers.* 2005;20:571-83.

(56) References Cited

OTHER PUBLICATIONS

Wang X, Li J, Wang Y, Cho KJ, Kim G, Gjyrezi A, et al. HFT-T, a targeting nanoparticle, enhances specific delivery of paclitaxel to folate receptor-positive tumors. *ACS Nano.* Oct. 27, 2009;3(10):3165-74.

Wang X, Zhao G, Van S, Jiang N, Yu L, Vera D, et al. "Pharmacokinetics and tissue distribution of PGG-paclitaxel, a novel macromolecular formulation of paclitaxel, in nu/nu mice bearing NCI-460 lung cancer xenografts". *Cancer Chemother Pharmacol.* Feb. 2010;65(3):515-26.

Wijsman JH, Jonker RR, Keijzer R, van de Velde CJ, Cornelisse CJ, van Dierendonck JH. "A new method to detect apoptosis in paraffin sections: in situ end-labeling of fragmented DNA ". J Histochem Cytochem. Jan. 1993;41(1):7-12.

Yamaoka T, Tabata Y, Ikada Y., "Distribution and tissue uptake of poly(ethylene glycol) with different molecular weights after intravenous administration to mice".*J Pharm Sci.* Apr. 1994;83(4):601-6.

Yuan F, Dellian M, Fukumura D, Leunig M, Berk DA, Torchilin VP, et al. "Vascular permeability in a human tumor xenograft: molecular size dependence and cutoff size". *Cancer Res.* Sep. 1, 1995;55(17):3752-6.

Yvon AM, Wadsworth P, Jordan MA. "Taxol suppresses dynamics of individual microtubules in living human tumor cells". *Mol Biol Cell.* Apr. 1999;10(4):947-59.

Zhang X, Jackson JK, Burt HM. "Determination of surfactant critical micelle concentration by a novel fluorescence depolarization technique". *J Biochem Biophys Methods.* Feb. 5, 1996;31(34):145-50.

\* cited by examiner

Tumor: H&E (40 and 400X)

Tumor: TUNEL – 40X

Tumor: Ki67 – 40X

Tumor: CD31 – 40X

CELLULOSE-BASED NANOPARTICLES FOR DRUG DELIVERY

The present application claims the priority benefit of U.S. provisional application No. 61/438,842, filed Feb. 2, 2011, the entire contents of which are incorporated herein by reference.

BACKGROUND OF THE INVENTION

1. Field of the Invention

This invention relates to the field of nanoparticles and, more specifically, to cellulose-based nanoparticles for drug delivery.

2. Description of Related Art

In the field of controlled drug delivery, the use of polymers to enhance solubility, pharmacodynamics (PK), pharmacodynamics (PD), bioavailability, efficacy, and decrease systemic toxicity is largely defined as polymeric therapeutics[1-2]. The generalized model of polymer therapeutics is attributed to Ringsdorf[3], a model he proposed in 1975, wherein a polymer architecture is modified by solubilizers, drugs, and disease targeting ligands to more effectively dissolve hydrophobic drugs and delivery them in a focused manner.

One rationale for polymer therapeutics is built around the observation that soluble macomolecules with molecular weights (MW) above 30-40 kDa circulate longer in the bloodstream, due to reduced glomular filtration and renal clearance[4-6]. In 1986, Matsumura and Maeda introduced their observation that tumor vasculature is highly permeable, and that higher MW polymers or particles would selectively accumulate in these tissues as a result.[7] It was found that nascent blood vessels in malignant tissues contain gaps through which particles can extravasate[8-9], and furthermore, lymphatic drainage in tumors is usually absent: particles can readily enter but not exit the tumor compartment.[10-11] Typically, particles smaller than 150-400 nm effectively migrate by the enhanced permeability and retention (EPR) effect, although preferably particles are less than 200 nm in size.[12] The discovery of the EPR effect provided significant impetus to develop polymer therapeutics, and in particular gave rise to nanomedicine, where multi-molecule structures comprising liposomes[13-15], polymeric micelles[16-18], polymersomes[19-21] and dendrimers[22-24] could effectively deliver drug through this passive targeting effect.[25]

One important rationale for development of nanoparticles was protection of drugs from metabolism by minimizing interaction of the drug with metabolic processes (improved PD profile).[26] In terms of PK however, particles themselves can be opsonized and cleared in the RES (bone marrow, liver, and spleen), reducing the effectiveness of these delivery systems.[13, 27] A solution to the RES clearance issue was pegylation: PEG chains conjugated to a polymer or nanoparticle prevent interaction of opsonins with the underlying chemistry through steric hindrance and reduction of hydrophobic and electrostatic interactions, minimizing recognition and clearance of the particle in the RES.[28-30] Pegylation became a common element in polymer therapeutics and nanomedicine.[13, 31]

In addition to adding stealth properties, particles can be functionalized with targeting ligands to promote the cellular internalization of nanoparticles to specific tissues over-expressing specific receptors, such as folate[32], RGD[33] and HER2[34]. Although investigators have invested heavily in these studies, limited success with specific targeting has been achieved in drug-delivery products, as tumor accumulation of nanoparticles is largely governed by the EPR effect.[35] It has been documented that targeting ligands can increase the blood clearance of the particles,[36-37] and that particles internalized though receptor recognition are trapped in the endosome/lysosome organelles and drug is often degraded.[38] More successful from a practical point of view has been the incorporation of imaging contrast agents into nanoparticles to enable real-time visualization of the particle (and drug) distribution in the physiology, permitting sensitive non-destructive measurement of biodistribution, and giving rise the field of personalized medicine and theranostics.[39-40] For example, superparamagnetic iron oxide nanoparticles (SPIONS) will selectively accumulate in tumors by the EPR effect, and provide MRI contrast.[41] Liposomes and polymeric micelles can be loaded with gadolinium compounds, which like SPIONS, provide MRI contrast.[42] Polymers can also be labeled with tracers such as [111]Indium for microSPECT analysis[43], or with dyes such as Cy5.5 for fluorescence imaging.[44]

Within the class of polymer micelles, hydrophobic drugs such as paclitaxel (PTX) can be loaded non-covalently in the core of micelle-forming polymers. Notable within this field are the PEG-PLA micelles (Genexol, now in Phase II clinical trials),[45] and NK105, a PEG-aspartic acid formulation.[45] Both Genexol and NK105 PTX micelle formulations improve upon administration of PTX alone, by reducing formulation toxicity through elimination of the Cremophor-based PTX delivery vehicle which causes hypersensitivity issues in human patients. In comparison to Genexol and NK105, Opaxio (also known as Xyotax and Polyglumex) is a polyglutamic acid polymer conjugated to PTX. Opaxio is in Phase III clinical trials, and to date, represents a promising candidate for approval. When examining the PK data for PTX (free drug), NK105 (micelle), Genexol (micelle), and Opaxio (conjugate), the half lives were 13.3, 10.6, 11.4, and 120 hours respectively, for doses of 210, 150, 300, and 233 mg/m$^2$.[16] The PK profile of the non-covalent NK105 and Genexol formulations were nearly identical to that of free PTX, whereas the Opaxio polymer conjugate was the only mode by which PK could be substantially improved. Hydrophobic drugs such as PTX and docetaxel (DTX) will partition from the micelle to plasma proteins including albumin and alpha-1-acid glycoprotein, rapidly depleting the nanoparticle of the drug content.[46] Therefore, dramatic improvements to PK and efficacy are likely to be seen only with polymer conjugates.

Currently, the most advanced polymer conjugates (those in clinical trials or approved) are formulated around albumin (Abraxane), HPMA (hydroxypropyl methacrylamide), PEG, polyglutamic acid, with a few other selected examples.[1, 47] This is not a long list of polymer compositions despite more than 30 years of research, and the limited selection reflects the cost and complications involved in synthesizing and identifying biocompatible biomaterials. Failure of candidate polymer can occur in a wide variety of modes, including foreign body response,[48] toxicity,[49] or instability in the biological milieu of hydrolytic enzymes and inflammatory processes.[50] Nanoparticle approaches can minimize these complications, as polymer conjugates can be designed to self assemble into structures which present a PEG chemistry (or other suitable shielding entities) to the biological environment, and minimize biological recognition or interaction with the core polymer and drug cargo.[27]

Certain classes of polysaccharides are approved as excipients for oral, transcutaneous, and parenteral drug administration,[51] but when referenced against the synthetic polymer field, comparatively little work has been done with these biocompatible polysaccharides in the contemporary nanoparticle drug delivery field, and most work has focused on chitosan-based materials.[52-55] Cera and co-workers conjugated doxorubicin (DOX) and daunomycin to carboxymethyl cellulose (CMC) and hyaluronic acid (HA), and reported that these compounds were toxic to cells in vitro, but with lower potency compared to the free drug. In addition, the degree of CMC acid group substitution with doxorubicin was low (9%), and this group did not follow up with reports on in vivo efficacy.[56] Uglea et al conjugated benzocaine to CMC and oxidized CMC, and tested the effects of these polymers on s.c. sarcoma tumors in rat models, and reported some anti-tumor effect from a single i.p. injection.[57] Auzenne et al conjugated paclitaxel (PTX) to HA, and performed in vitro and in vivo efficacy assays.[58] Mice were implanted with ovarian carcinoma xenografts in the peritoneal cavity, and were treated with an intraperitoneal injection of 200 mg/kg PTX-HA, a treatment which effectively cured the mice and was well tolerated. There have been no reports regarding the activity of this compound against other solid tumours. Inoue et al reported on a camptothecin analog (DX-8591) conjugated to a carboxymethyldextran via a peptide spacer, which demonstrated strong action against tumours in mice models, and has been tested in 27 patients in a Phase I trial with 1 patient experiencing complete remission, 1 patient experiencing partial remission, and 14 patients experiencing disease stabilization.[59-60] In short, while the class of polymer is well known, successful uses of carboxymethyl cellulose for nanoparticle technologies are quite limited.

A substantial fraction of therapeutic small molecules are hydrophobic,[61] and rendering these water soluble is, as indicated, a significant rationale behind the development of polymer therapeutics. The taxanes in particular have received special attention, as PTX and DTX command a significant share of the pharmaceutical market, and are currently formulated with Cremophor EL-P/ethanol/saline[62] and Tween80/ethanol/saline respectively, each of which causes hypersensitivity reactions, requiring pre-medication of patients being treated with PTX or DTX.[63-64] Abraxane (albumin-PTX) and Opaxio (polyglutamic acid-PTX) represent the most advanced PTX conjugates to date, with Abraxane approved for use in the US, and Opaxio in Phase III clinical trials for non-small cell lung cancer[47]. However, DTX is replacing PTX in clinical applications due to enhanced action,[65] and reports on DTX conjugates are indicating that DTX can be more effectively and safely delivered as a polymer conjugate.[66-68]

SUMMARY OF THE INVENTION

In one aspect, there is provided a compound comprising an acetylated carboxymethylcellulose (CMC-Ac) covalently linked to: at least one poly(ethylene glycol) (PEG), and at least one hydrophobic drug.

In another aspect, there is provided a self-assembling nanoparticle composition comprising the compound described herein. Preferably, the composition has a critical micelle concentration (cmc) of about 0.1 mg/mL.

In a further aspect, there is provided a pharmaceutical composition comprising the self-assembling nanoparticle composition described herein and a pharmaceutically acceptable carrier and/or diluent.

In a further aspect, there is a method for providing sustained-release delivery of a hydrophobic drug to a patient in need thereof comprising administering to the patient an effective amount of the self-assembling nanoparticle composition as described.

In a further aspect, there is a method of treating cancer in a patient in need thereof, comprising administering to said patient an effective amount of a self-assembling nanoparticle composition comprising the compound described herein. Preferably, the cancer is selected from breast cancer, lung cancer, metastatic cancer, and pancreatic cancer.

In a further aspect, there is provided a process for preparing a self-assembling nanoparticle composition comprising:

covalently linking at least one PEG and at least one hydrophobic drug to a CMC-Ac;

isolating the product of step (a);

dissolving the isolated product of step (b) in a suitable organic solvent, preferably DMF or DMSO and further preferably THF or acetonitrile, to form a solution;

adding the solution of step (c) dropwise to an aqueous solution under conditions suitable for forming the self-assembling nanoparticle composition.

In a further aspect, there is provided a compound represented by the formula:

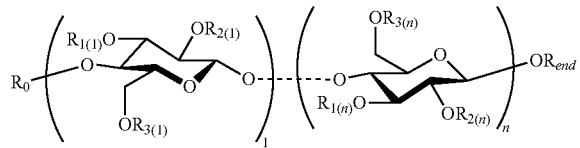

wherein $R_0$, $R_{1(1)}$ ... $R_{1(n)}$, $R_{2(1)}$ ... $R_{2(n)}$, $R_{3(1)}$ ... $R_{3(n)}$, and $R_{end}$ are each independently selected from:

(a) acetyl;

(b)

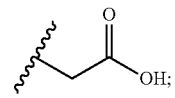

(c)

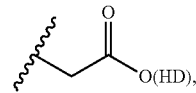

wherein —O(HD) represents a hydrophobic drug having a point of attachment via a hydroxyl group; or (d)

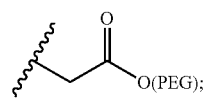

and n is an integer >94.

BRIEF DESCRIPTION OF THE DRAWINGS

Embodiments of the invention may best be understood by referring to the following description and accompanying drawings. In the drawings.

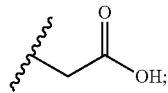

(c)

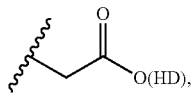

wherein —O(HD) represents a hydrophobic drug having a point of attachment via a hydroxyl group; or
(d)

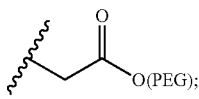

and
n is an integer >94.

Figure 1:
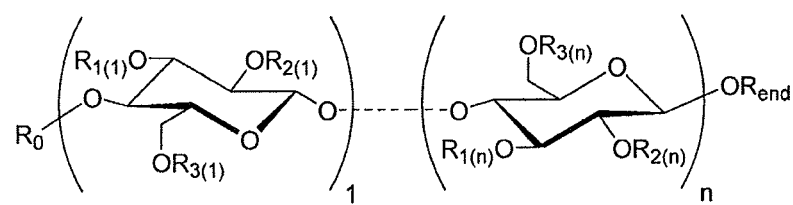
FIG. 1 shows a schematic of a polymer conjugate according to one aspect, wherein $R_0$, $R_{1(1)} \ldots R_{1(n)}$, $R_{2(1)} \ldots R_{2(n)}$, $R_{3(1)} \ldots R_{3(n)}$, and $R_{end}$ are each independently selected from:
(a) acetyl;
(b)
Figure 2:
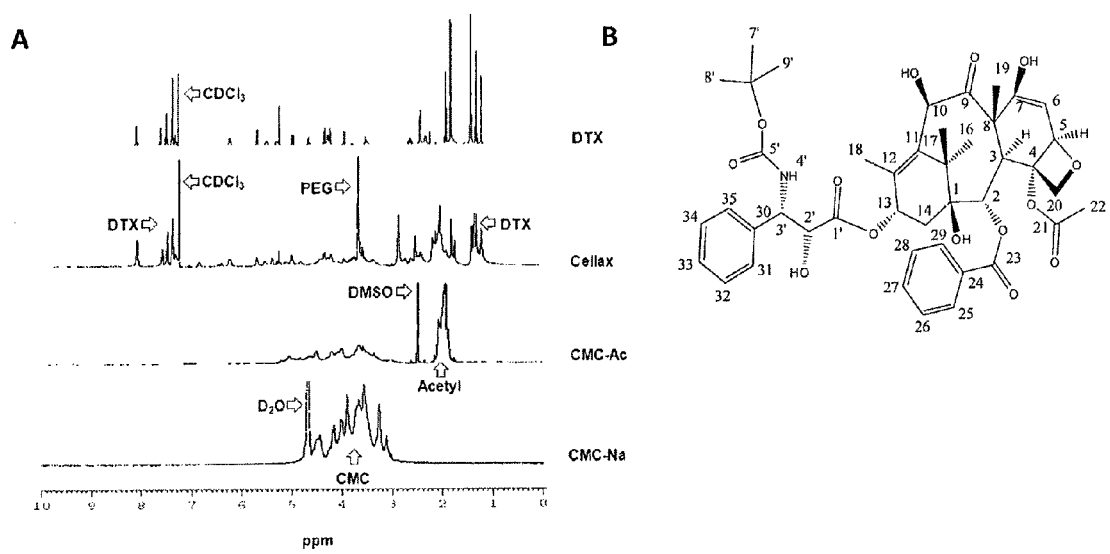

FIG. 2 shows the $^1$H NMR of Cellax and Components. A: Spectra of DTX, sodium carboxymethylcellulose (CMC-Na), acetylated CMC, and the Cellax product. B: DTX with the carbon numbering scheme.

Figure 3:
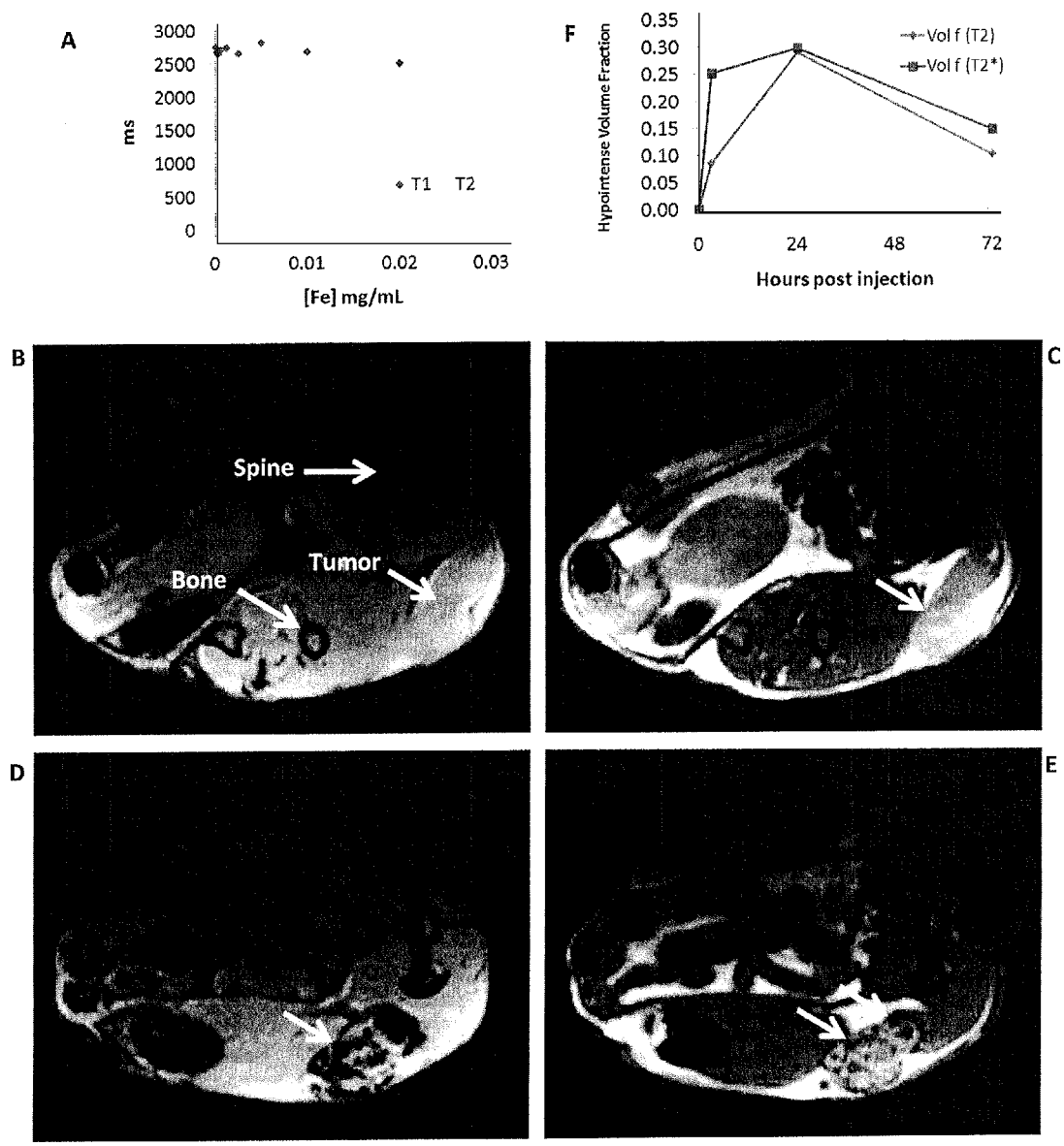

FIG. 3 shows (A) Analysis of T1 and T2 signal for Cellax-SPIONS in vitro. MRI analysis of mice bearing EMT-6 flank tumors, and treated with Cellax-SPION (10 mg Fe/kg, 133 mg/kg DTX). (B) Pre-injection T2* scan, (C) pre-injection T2 scan, (D) 3-hour post-injection T2* scan, (E) 3-hour post-injection T2 scan. The tumor volume can be differentiated from the neighboring tissues in the background scans, and substantial development of MR contrast due to the SPION susceptibility artifact. (F): calculation of hypointense volume fractions by MIPAV image analysis, wherein hypointense voxels are defined as having an intensity below that of 5 SD standard deviation of the mean intensity of neighboring muscle.

Figure 4:
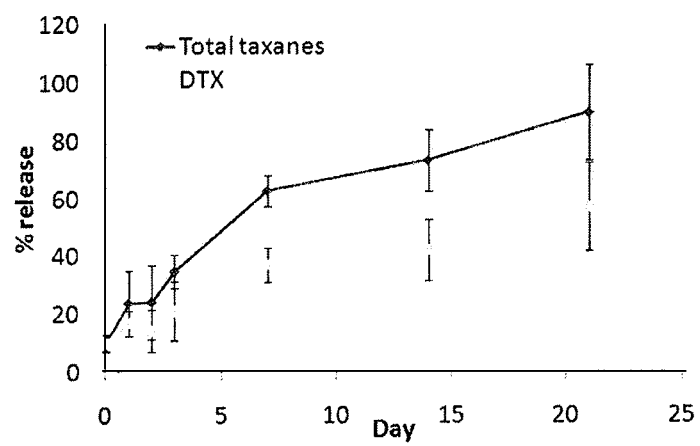

FIG. 4 shows the release of DTX from Cellax particles in FBS containing saline (50 vol %). Particles were incubated at 37° C. in a 5% $CO_2$ atmosphere. At selected timepoints samples were extracted and analyzed by HPLC. Two peaks were detected: DTX and 7-epidocetaxol. Total taxanes in the plot refers to the combined release of DTX and the isomer, and indicates when full release had been reached.

Figure 5:
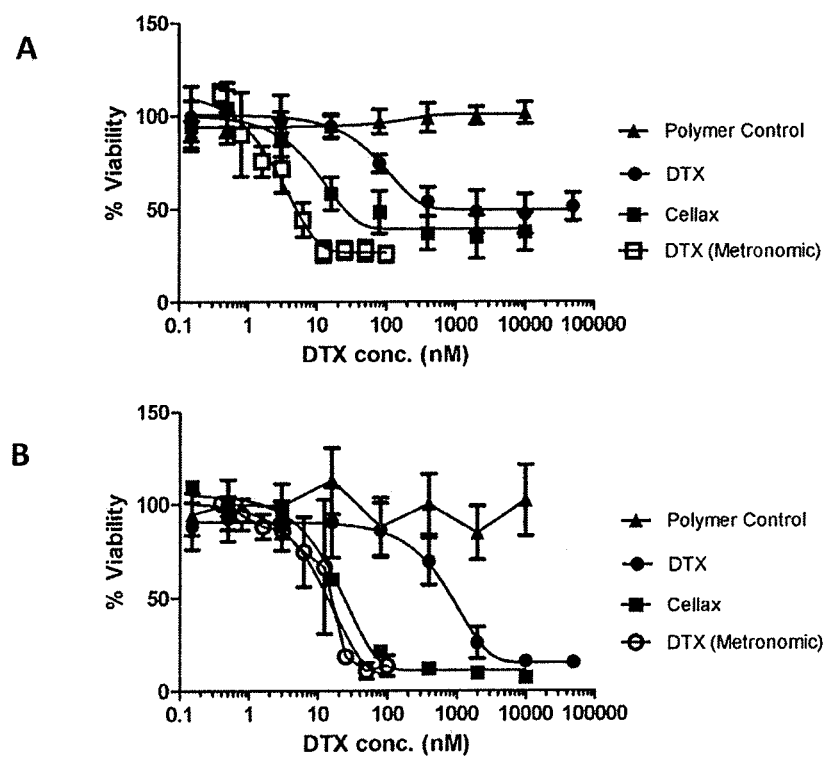

FIG. 5 shows the IC50 analysis of DTX toxicity. A: EMT-6 B: LL/2. Cells were cultured on tissue culture polystyrene (1000 cell/well) for 1 day, followed by addition of media containing DTX, Cellax, or drug-free polymer controls. Polymer controls at each selected DTX concentration are matched to the Cellax sample by weight concentration (mg/mL). For metronomic treatment of free DTX, the dose was administered in four parts over two days. Cultures were maintained for 2-3 days, until the no-treatment control wells approached confluence. Cell viability was determined by the XTT assay, with no-cell background signal being subtracted. IC50 curves were calculated in GraphPad Pro. Each group was n=9, and error bars are ±standard deviation.

Figure 6:
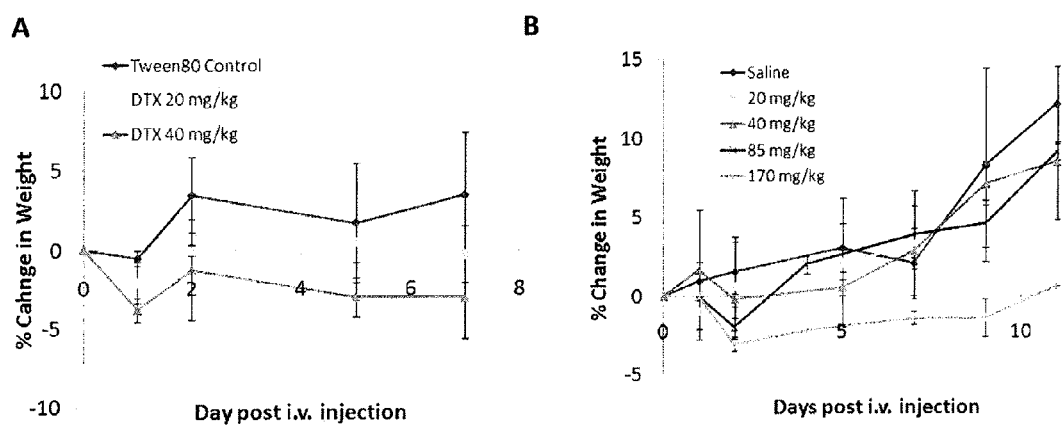

FIG. 6 shows the toxicity assay (maximum tolerated dose) analysis of DTX and Cellax in Balb/c mice. Healthy tumor-free mice were injected with DTX (in a Tween80/ethanol/saline 20:13:67 carrier) or Cellax (0.9% saline). Body weight was measured regularly, and the limiting toxic dose was set by <5% body weight loss. Cellax reaches a maximum concentration of 15 mg/mL DTX (170 mg/kg), so a true MTD is not known.

Figure 7:
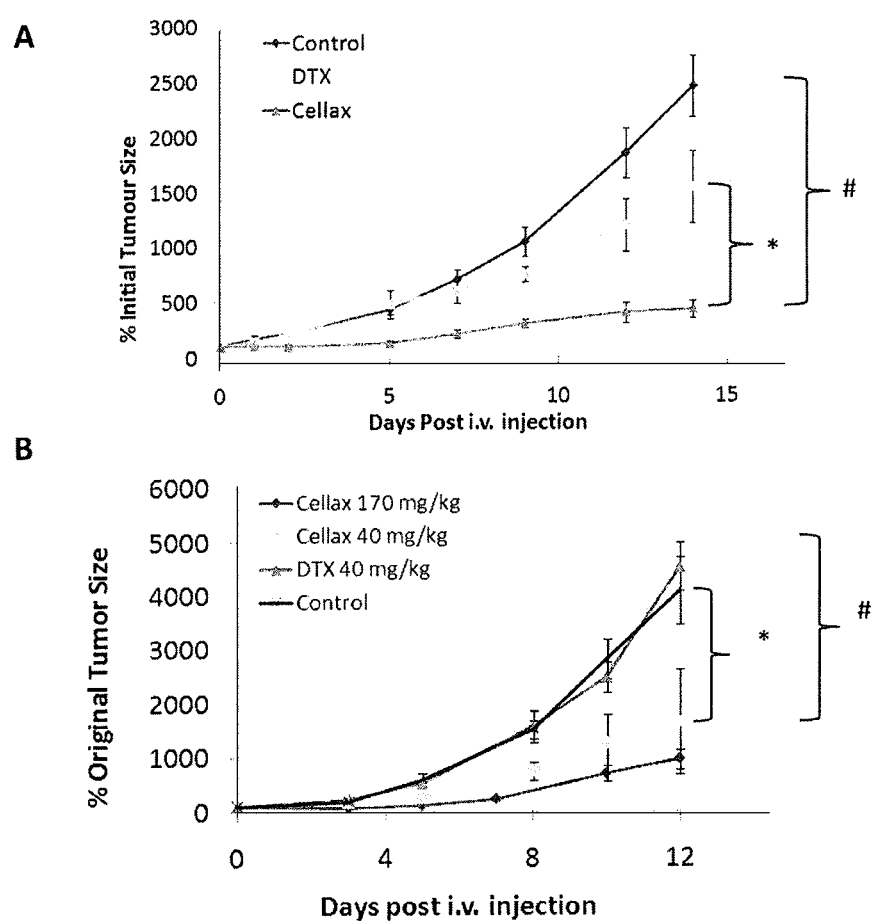

FIG. 7 shows the efficacy of the DTX and Cellax treatments on mice carrying syngeneic flank tumors. DTX was formulated in Tween80/ethanol/saline, and Cellax was formulated in 0.9% saline. Control mice were treated with saline. (A) Efficacy study with Balb/c mice and EMT-6 flank model with 40 mg/kg DTX dosing (B) Efficacy study with C57/BL6 mice and LL/2 flank model with 40 and 170 mg/kg DTX dosing. # p<0.001, * p<0.05, n=6 per group. Error bars are standard deviation.

Figure 8A:
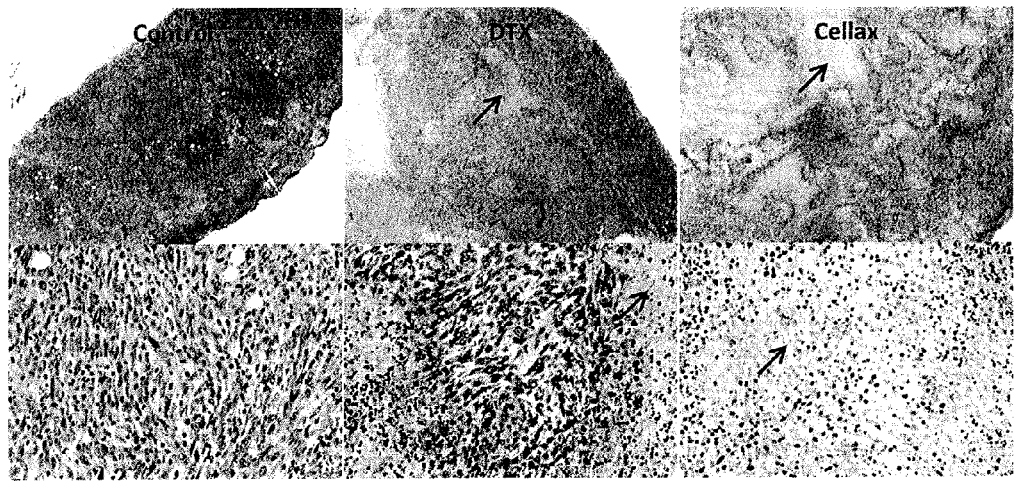
Figure 8A:
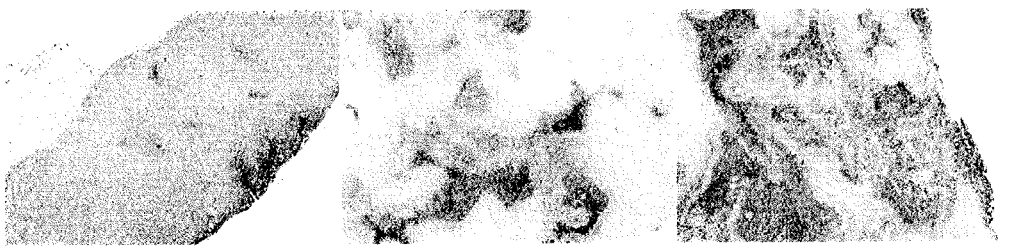
Figure 8A:
Figure 8A:
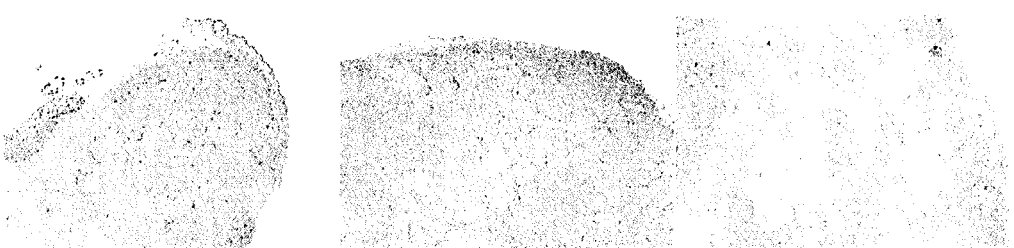

FIG. 8A shows the histological and immunohistological analysis of EMT-6 tumors in Balb/c mice. Left column: control mice. Middle column: DTX (40 mg/kg) treated mice. Right column: Cellax (40 mg DTX/kg) treated mice. In the H&E stained sections (40 and 400×), evidence of necrosis is marked with arrows, and is particularly evident in Cellax treated tumors. TUNEL staining (40×): indication of apoptosis is evident in all samples, but is markedly greater in the Cellax-treated tumor, and the morphology of the stained regions is similar to the necrotic regions in the H&E stained sections. Ki67 staining (40×): regions of the DTX and Cellax treated tumors are devoid of cell replication events, and these regions are congruent to the H&E and TUNEL images. CD31 staining (40×): angiogenesis activity in the DTX-treated and especially in the Cellax-treated tumors is reduced, especially in the regions already identified in the H&E, TUNEL, and Ki67 analyses.

Figure 8B:
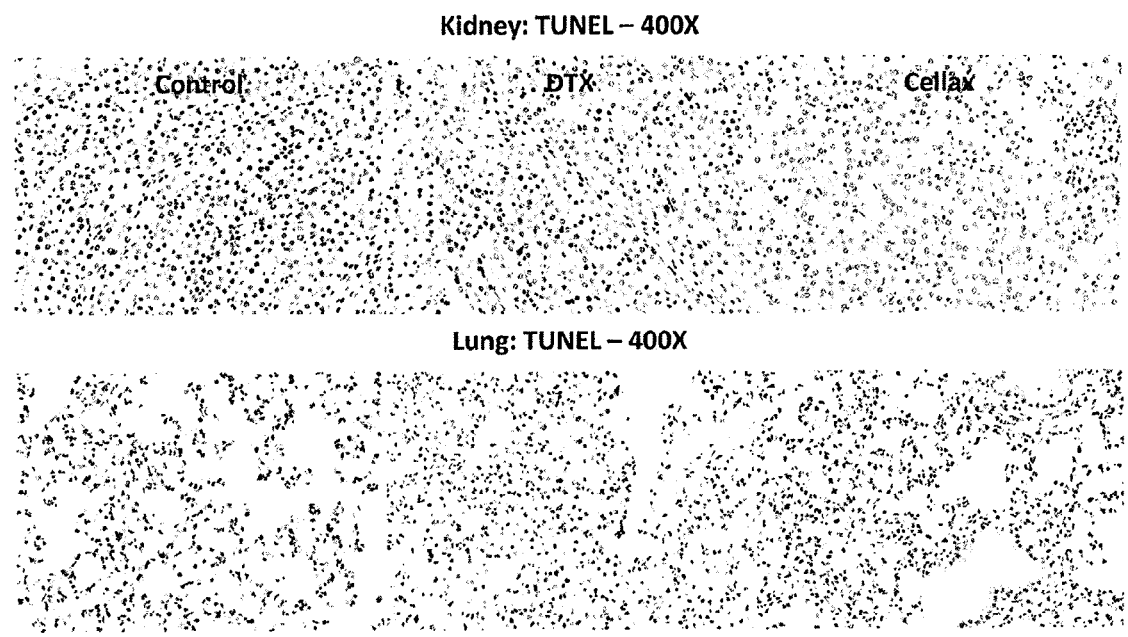

FIG. 8B shows the immunohistological analysis of the kidney and lungs of Balb/c mice (carrying EMT-6 flank tumors) treated with saline, DTX (40 mg/kg) and Cellax (40 mg DTX/kg). Images are 400× magnification. Note the presence of positive TUNEL staining in the DTX-treated mice, and the absence of staining in control and Cellax-treated mice.

Figure 9:
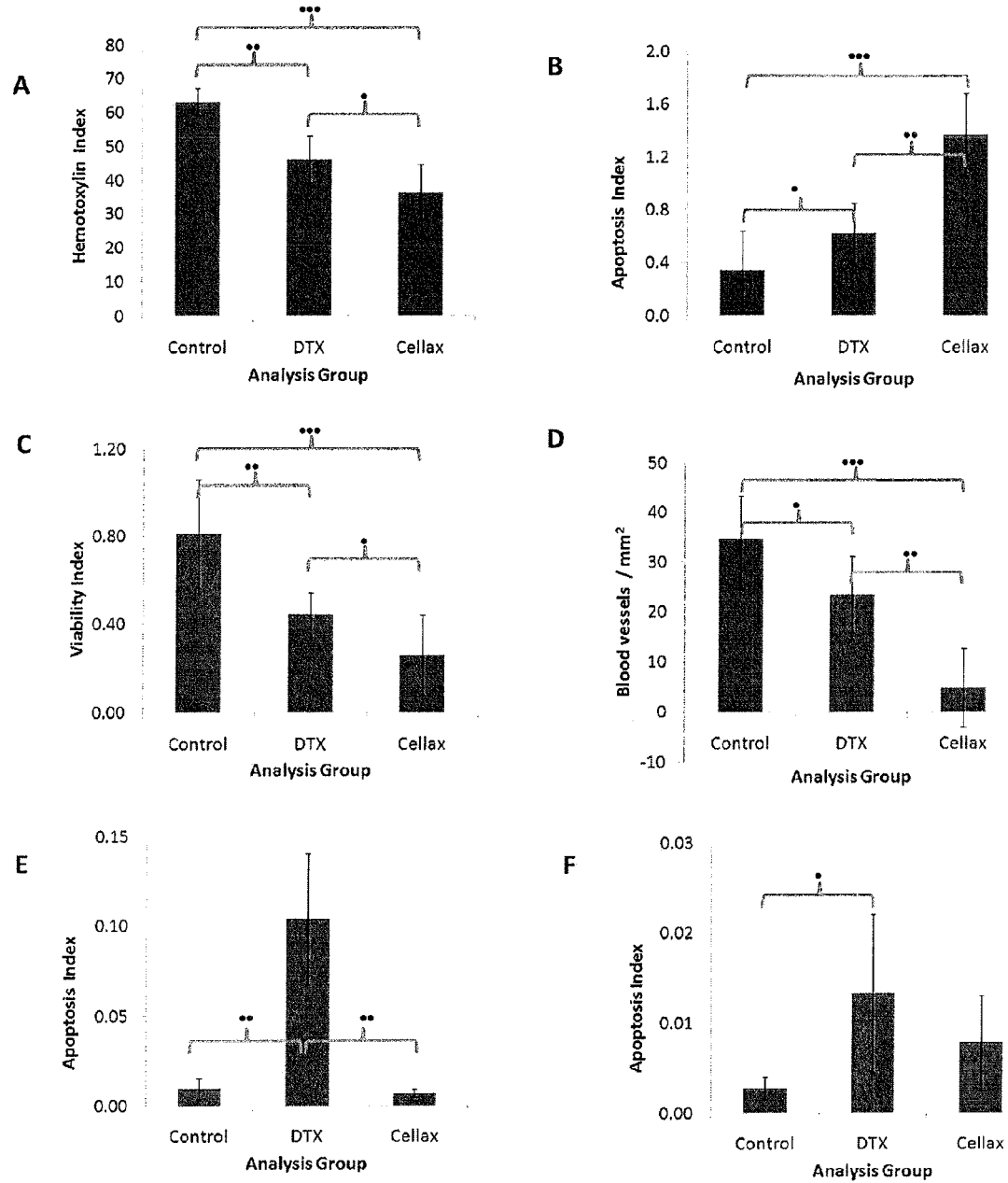

FIG. 9 shows tumor histology: quantification of stains (A) Hemotoxylin staining of tumors (B) TUNEL staining of tumors (C) Ki67 staining of tumors (D) CD31 staining of tumors (E) TUNEL staining in kidneys (F) TUNEL staining in lungs. • p<0.05, •• p<0.001, ••• p<0.0001.

Figure 10:
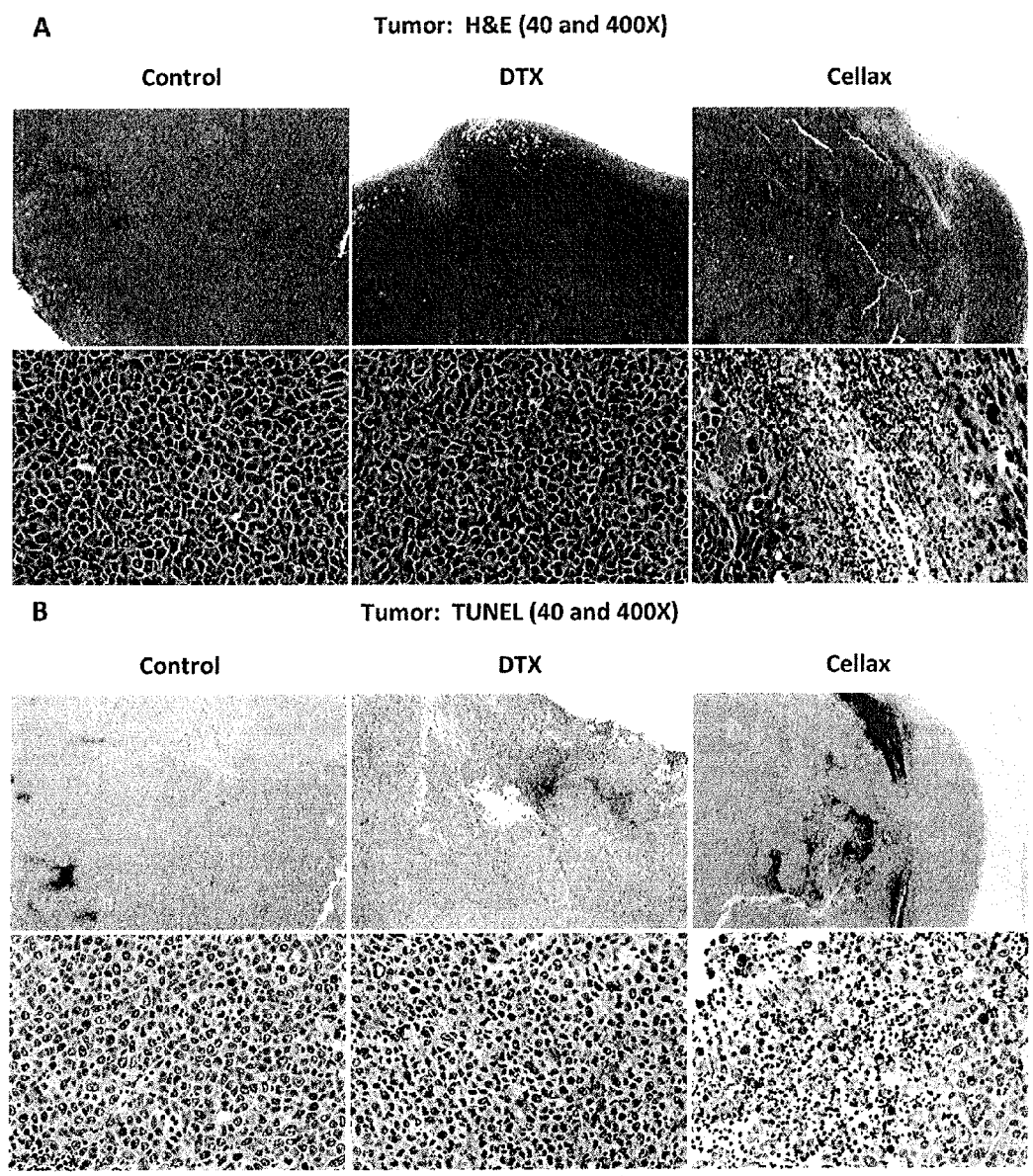

FIG. 10 shows tumor histology for the LL/2 model in C57/BL6 mice: (A) H&E staining, (B) TUNEL staining.

Figure 11:
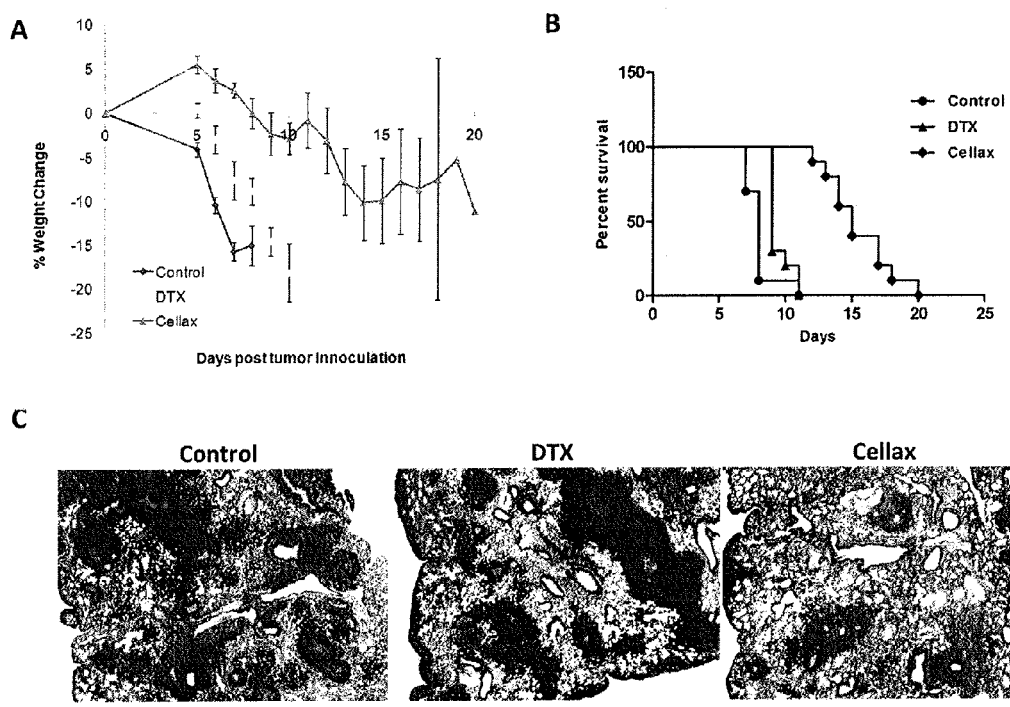

FIG. 11 shows (A) Weight loss experienced by Balb/c mice inoculated with EMT-6 cells by i.v. injection. Error bars represent SE, and marker that lack error bars are n=1 (sole surviving mice). (B) Survival plot (C) H&E stained sections of control, DTX (40 mg/kg) and Cellax (40 mg DTX/kg) treated mice lungs.

Figure 12:
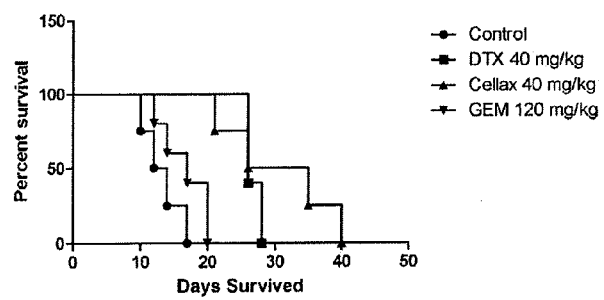

FIG. 12 shows survival patterns in C57/BL6 mice inoculated with PAN02 murine pancreatic cells ($2.5 \times 10^6$ cell/injection).

DETAILED DESCRIPTION OF THE PREFERRED EMBODIMENTS

In the following description, numerous specific details are set forth to provide a thorough understanding of the invention. However, it is understood that the invention may be practiced without these specific details.

Based on the survey of polymeric conjugate development to date, a functional polymeric nanoparticle preferably comprises the following attributes: (1) it dissolves or transports a hydrophobic drug in an aqueous environment, (2) the drug is protected from metabolism by the particle, (3) the particle is protected from RES elimination by PEG or other suitable chemistry, (4) the polymer self-assembles into a suitably scaled nanoparticle due to a balance in hydrophobic and hydrophilic elements, (5) the particle accumulates in the targeted disease compartment through passive accumulation (6) the link between the drug and particle is reversible, so that the drug can be released and (7) the polymer is biocompatible, and (8) the particle contains an agent to provide imaging contrast or detection in the physiological system. One objective was to engineer a cellulose-based composition to deliver a hydrophobic drug, preferably DTX, the design of which would preferably address the major design elements described above.

In one aspect, there is provided a compound comprising an acetylated carboxymethylcellulose (CMC-Ac) covalently linked to: at least one poly(ethylene glycol) (PEG), and at least one hydrophobic drug. In one embodiment, the covalent linkages are ester linkages.

Those of skill in the art will understand that each of the hydrophobic drug and PEG may be covalently linked to the CMC-Ac by a direct linkage between a carboxylic acid residue of the CMC-Ac and a functional group of the hydrophobic drug and PEG (e.g. a hydroxyl group), or by an indirect linkage via one or more bifunctional linkers. Preferred linkers are those that are biodegradable, non-toxic when cleaved from the conjugate, and are relatively stable to hydrolysis in the circulation.

In a preferred embodiment, the hydrophobic drug is an anticancer agent (i.e. an anti-proliferative, anti-neoplastic, or chemotherapeutic agent to prevent or treat tumours), preferably one of docetaxel, camptothecin and paclitaxel.

In some embodiments, the at least one PEG is poly(ethylene glycol) methyl ether (mPEG) having an average $M_n$ of between about 550 and about 10,000, preferably about 2000.

In some embodiments, the CMC consists of between about 95 and 3600 monomer units, preferably about 3500 monomer units.

In some embodiments, the molar ratio of (CMC-Ac acetyl groups):(CMC-Ac carboxylic acid groups/PEG/hydrophobic drug) is between about 2.5:0.5-1.8:1.2, preferably about 2.18: 0.82. Preferably, the mPEG is present in an amount of about 3.5-22.7 weight %, and the docetaxel is present in an amount of about 22.5-43.3 weight %, further preferably, in PEG is present in the amount of 4.7-5.3 weight %, and the docetaxel is present in an amount of about 30.1-39.5 weight %, and further preferably, PEG is present in an amount of 4.7 weight %, and the docetaxel is present in an amount of 36.9 weight %.

In some embodiments, the molar ratio of mPEG:docetaxel: (CMC-Ac carboxylic acid groups) is from about 0.9:13.4: 85.7 to about 5.4:26.4:68.2, as estimated by $^1$H NMR analysis, preferably from about 1:15.1:83.6 to about 1.1:23.7:75.3, further preferably 1:20.5:78.5.

In some embodiments, the CMC-Ac is further covalently linked to at least one imaging agent, preferably Cy5.5.

In another aspect, there is provided a self-assembling nanoparticle composition comprising the compound described herein. Preferably, the composition has a critical micelle concentration (cmc) of about 0.1 mg/mL.

In some embodiments, the self-assembling nanoparticle composition of claim 14 or 15, wherein the nanoparticles have an average diameter of about 49-278 nm and/or a complete range of 16-396 nm.

In some embodiments, the self-assembling nanoparticle composition described herein further comprising at least one hydrophobic agent encapsulated therein, preferably selected from either an imaging agent or a therapeutic agent. Preferably, the at least one imaging agent is a superparamagnetic iron oxide nanoparticle (SPION), preferably between 7-30 weight % SPION, and more preferably about 30 weight % SPION.

In a further aspect, there is provided a pharmaceutical composition comprising the self-assembling nanoparticle composition described herein and a pharmaceutically acceptable carrier and/or diluent.

Acceptable carriers and diluents would be known to a person skilled in the art. Generally, such carriers should be nontoxic to recipients at the dosages and concentrations employed.

In a further aspect, there is a method for providing sustained-release delivery of a hydrophobic drug to a patient in need thereof comprising administering to the patient an effective amount of the self-assembling nanoparticle composition as described.

In a further aspect, there is a method of treating cancer in a patient in need thereof, comprising administering to said patient an effective amount of a self-assembling nanoparticle composition comprising the compound described herein. Preferably, the cancer is selected from breast cancer, lung cancer, metastatic cancer, and pancreatic cancer.

In a further aspect, there is provided a process for preparing a self-assembling nanoparticle composition comprising:

covalently linking at least one PEG and at least one hydrophobic drug to a CMC-Ac;

isolating the product of step (a);

dissolving the isolated product of step (b) in a suitable organic solvent, preferably DMF or DMSO and further preferably THF or acetonitrile, to form a solution;

adding the solution of step (c) dropwise to an aqueous solution under conditions suitable for forming the self-assembling nanoparticle composition.

Preferably, the covalent linkages are ester linkages.

The processes described herein are generally useful for preparing conjugates of CMC-Ac with any PEG and any hydrophobic drugs that are appropriately functionalized for linking to the CMC-Ac, as described herein.

Suitable solvents for use in the processes of the present invention include those solvents that are inert under the conditions of the reaction/procedure being described in conjunction therewith.

In some embodiments, said suitable conditions in step (d) comprise vigorously mixing said aqueous solution during the dropwise addition of the solution of step (c).

In some embodiments, the solution of step (c) has a concentration of 10-25 mg/mL. Preferably, the solution of step (c) has a concentration of 10 mg/mL.

In some embodiments, step (d) comprises a 10-fold dilution of the solution of step (c) once the addition to the aqueous solution is complete.

In some embodiments, the aqueous solution of step (d) is selected from 0.9% NaCl, 10% sucrose, or water.

In some embodiments, the organic solvent in step (c) is selected from acetonitrile ($CH_3CN$) or tetrahydrofuran (THF), preferably $CH_3CN$.

In some embodiments, step (b) comprises precipitation of the product of step (a) using ether, and washing the precipitate with water.

In some embodiments, the process further comprises isolating the self-assembling nanoparticle composition formed in step (d) via dialysis and/or filtration.

In preferable embodiments, the at least one hydrophobic drug is one of docetaxel, camptothecin and paclitaxel. Preferably, the CMC-Ac is prepared via acetylation of a carboxymethyl cellulose with a degree of substitution (DS) of between about 0.75 and about 0.85, preferably about 0.82. Further preferably, the at least one PEG is poly(ethylene glycol) methyl ether (mPEG) having an average $M_n$ of between about 550 and about 10,000, preferably about 2000.

In one embodiment, step (a) comprises providing the mPEG in an amount of about 30 mol % and providing the docetaxel in an amount of about 40-50 mol %, relative to the carboxylic acid groups of said CMC-Ac, preferably about 40 mol % or 50 mol %.

In some embodiments, the solution of step (c) further comprises at least one hydrophobic agent encapsulated therein, preferably selected from either an imaging agent or a therapeutic agent. Preferably, the at least one imaging agent is a superparamagnetic iron oxide nanoparticle (SPION).

Preferably, the organic solvent in step (c) is THF.

In some embodiments, the at least one imaging agent is present in the solution of step (c) in an amount of about 9-50 weight %, based on the combined weight of the at least one imaging agent and the isolated product of step (b).

In a further aspect, there is provided a compound represented by the formula:

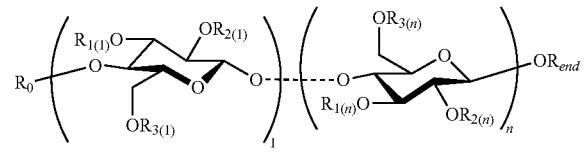

wherein $R_0$, $R_{1(1)} \ldots R_{1(n)}$, $R_{2(1)} \ldots R_{2(n)}$, $R_{3(1)} \ldots R_{3(n)}$, and $R_{end}$ are each independently selected from:

(a) acetyl;

(b)

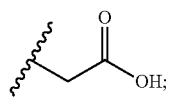

(c)

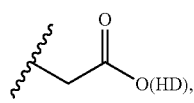

wherein —O(HD) represents a hydrophobic drug having a point of attachment via a hydroxyl group; or (d)

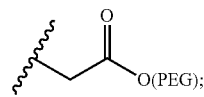

and n is an integer >94.

Preferably, the ratio of (a):(b+c+d) is about 2.18:0.82. Also preferably, n is between about 95 and 3600 monomer units, preferably about 3500.

It will be appreciated by those of skill in the art that the actual preferred amounts of active agent in a specific case will vary according to the particular formulation and manner of administration. The specific dose for a particular individual depends on age, body weight, the severity of the particular disorder to which the therapy is applied, and other factors. Dosages for a given subject can be determined using conventional considerations.

The following examples are illustrative of various aspects of the invention, and do not limit the broad aspects of the invention as disclosed herein.

EXAMPLES

Materials and Methods

Sodium carboxymethylcellulose (CEKOL 30K (DS)= 0.82) was obtained from CPKelco (Atlanta, Ga., USA), and is an FDA and EU food grade material. Glacial acetic acid, acetic anhydride, sulphuric acid, acetone, acetonitrile, poly(ethylene glycol) methyl ether (mPEG-OH, MN=2000), 1-ethyl-3-(3-dimethylaminopropyl)-carbodiimide HCl (EDC HCL), N-hydroxysuccinimide (NHS),4-dimethylaminopyridine (DMAP), and diethyl ether were purchased from Sigma Aldrich (Oakville, ON). Docetaxel (DTX) was purchased from LC Laboratories (Woburn, Mass., USA). Slide-a-Lyzer 10 and 20 kDa MWCO dialysis cartridges were purchased from Pierce Biotechnology (Rockford, Ill.). Vivaspin 10 kDa MWCO ultracentrifugation filters were purchased from Fisher (Ottawa, ON, Canada).

NMR Analysis

Samples were dissolved in deuterated chloroform ($CDCl_3$), deuterium oxide ($D_2O$) or N,N-dimethylsulphoxide (DMSO), and analyzed on a Bruker 500 instrument. Spectra were processed using TOPSpin software.

HPLC, HPLC/MS, and GPC Analysis

DTX analysis was performed on an HPLC system consisting of a Waters e2696 Separation Module, 2414 RI and 2998 PDA detectors, and operated by Empower Pro 2 software. The samples were injected onto an Agilent XDB-C18 column (1.8 μm, 4.6×50 mm) column with 0.35 mL/min 95/5 acetonitrile/water isocratic program. The method for analysis and detection of taxanes was derived from several published reports,[69-71] adapted for the instrumentation in the lab. For routine analysis, known taxane identities (docetaxel, paclitaxel, and 7-epidocetaxel) were identified by PDA detector with a selected wavelength of 274 nm. During method development, samples were analyzed by a Waters Acquity HPLC/MS system equipped with a PDA and SQ MS detector. In these analyses, samples were injected on an Acquity HPLC BEH C18 column (1.7 μm, 2.1×50 mm), at a flowrate of 0.4 mL/min, with a gradient program of 95-10% water/acetonitrile over 5 minutes. Detection of DTX (and other products) were in ES+ mode. Polymers were analyzed by a GPC system consisting of a Waters e2696 Separation Module, 2414 RI and 2998 PDA detectors, and operated by Empower Pro 2 software. THF soluble samples were injected onto Waters Styragel HR5E and HR 3 columns (in series) with 0.35 mL/min THF flowrate. Water soluble samples were analyzed using a Waters Ultrahydrogel 1000 column with a 1 mL/min flowrate of water. Detection of free DTX and PEG was by PDA (274 nm) and RI respectively.

Calculation of Stoichiometry for the CMC Polymers.

The CMC-Na polymer is modified with carboxymethyl groups, and was supplied by the manufacturer with an analyzed DS value of 0.82: each galactose monomer unit contains 0.82 moles carboxylic acid and 2.18 moles hydroxyl. Therefore, the molecular weight of each monomer is approximated as: 162 g/mol (galactose)+(59.01 g/mol (acid group)× 0.82)=210 g/mol. These chemical composition values were used to calculate the stoichiometry of reactions performed on CMC polymers.

Acetylation of the CMC

The method for acetylation of CMC was adapted from a method reported by Namikoshi.[72] Sodium carboxymethylcellulose (CMC-Na CEKOL 30K, 10 g) was weighed into a round bottom flask, and was suspended in 20% sulphuric acid (200 mL) with vigorous stirring at room temperature for 2 hours. The slurry of CMC-COOH powder was washed with water until the water tested neutral, and then washed with 3×30 mL glacial acetic acid volume to ensure complete dehydration of the CMC-COOH. The CMC-COOH was transferred to a round bottom flask placed in an ice bath, and suspended in glacial acid (50 mL). Acetic anhydride (30 mL) and sulphuric acid (1.2 mL) were added to the chilled slurry, the temperature was then raised to 50° C., and the solution was vigorously stirred for three hours, or until clarified. The reaction solution was concentrated by rotary evaporation (58° C., 58 mbar) and was precipitated in deionized water. The water was exchanged via repeated filtrations until the water tested a neutral pH. The acetylated CMC (CMC-Ac) powder was dried under heavy vacuum overnight, dissolved in minimal acetone, and precipitated through water. The polymer was centrifuged out of solution, dried by lyophylization, and analyzed by H NMR in DMSO solvent.

Synthesis of Cellax

Preparation of the Cellax described throughout the manuscript is described here (50 mol % DTX feed, 30 mol % PEG feed, or 50/30), followed by related reactions detailing compositions that did not form acceptable particles. 50/30 Synthesis: acetylated carboxymethylcellulose (CMC-Ac, 300 mg, 1.5 mmol acid) was weighed into a 25 mL glass vial, and dissolved in MeCN (2 mL). EDC HCl (441 mg, 2.3 mmol) was dissolved in MeCN (12 mL) and water (0.5 mL). NHS (265 mg, 2.3 mmol) and DMAP (28 mg, 0.23 mmol) were dissolved in MeCN (1 mL). mPEG-OH (690 mg, 0.35 mmol) was dissolved in MeCN (2 mL) with mild heating. DTX (465 mg, 0.58 mmol) was dissolved in MeCN (12 mL) and DMF (1 mL). The EDC HCL, NHS, and DMAP reagents were added to the CMC-Ac solution, followed by addition of the mPEG-OH and the DTX. The solution was stirred overnight at room temperature with protection from light. The solvent was removed by rotary evaporation (55° C., 5 mbar), and the product (Cellax) was dissolved in MeCN (3 mL), and precipitated through 40 mL diethyl ether. The Cellax was dried, re-dissolved in MeCN, and the precipitation was repeated 2×. The solvent was removed by heavy vacuum, and the fine powder was washed with water (25 mL) and recovered by centrifugation. The Cellax product was analyzed by gel permeation chromatography for un-reacted PEG and DTX, and washing was repeated if residual reagent was detected. $^1$H NMR analysis (CDCl$_3$) was conducted to confirm the presence of DTX and PEG, and to estimate molecular composition. The feed ratio of DTX was varied while holding PEG constant to create a range of DTX content Cellax models. CMC-Ac (50 mg, 0.19 mmol acid) was activated with EDC HCl (75 mg, 0.39 mmol) and NHS (45 mg, 0.39 mmol) in the presence of DMAP (5 mg, 0.04 mmol), followed by the addition of varied DTX (16, 31, 47, 63, 142 mg, 0.02, 0.04, 0.06, 0.08, 0.18, mmol) and mPEG-OH (117 mg, 0.06 mmol). The feed ratio of PEG was varied while holding DTX constant to create a range of PEG content Cellax models. CMC-Ac (100 mg, 0.39 mmol acid) was activated with EDC HCl (224 mg, 1.17 mmol) and NHS (135 mg, 1.17 mmol) in the presence of DMAP (48 mg, 0.39 mmol), followed by the addition of varied PEG (78, 156, 390, 546, 780, 1169 mg, 0.04, 0.08, 0.19, 0.27, 0.39, 0.58 mmol) and DTX (157 mg, 0.19 mmol). All analogues were purified in the same manner as the preferred composition described above. Compounds were dissolved in CDCl$_3$ for $^1$H NMR analysis, and composition was estimated by integration of selected peaks.

Synthesis of CMC-Ac-PEG (Control Polymer)

A CMC-Ac-PEG control molecule was synthesized using the same conditions as described for Cellax. CMC-Ac (100 mg, 0.38 mmol acid) was reacted with mPEG$_{2000}$ (230 mg, 0.12 mmol) in the presence of EDC HCl (147 mg, 0.77 mmol), NHS (88 mg, 0.77 mmol), and DMAP (9 mg, 0.08 mmol) in acetonitrile solvent (6 mL). After overnight reaction, the solvent was removed by rotary evaporation (55° C., 5 mbar), dissolved in water (5 mL) and dialyzed against multiple exchanges of water using 20 kDa MWCO Slide-a-lyzer dialysis cartridges. The purified product was recovered by lyophylization, and analyzed by aqueous GPC to verify that un-reacted PEG had been entirely extracted. Analysis of chemical composition was performed by $^1$H NMR in D$_2$O.

Conjugation of DTX, Cy5.5, and PEG to CMC

PEG bisamine (169 mg, 0.084 mmol) was dissolved in acetonitrile (2 mL), to which was added DMAP (1 mg, 0.008 mmol) and Cy5.5 NHS ester (050 mg, 0.084 mmol, 0.5 mL acetonitrile). The solution was stirred for four hours at room temperature and protected from light. Acetylated carboxymethylcellulose (CMC-Ac, 100 mg, 0.39 mmol acid) was weighed into a 25 mL glass vial, and dissolved in MeCN (2 mL). EDC HCl (149 mg, 0.78 mmol) was dissolved in MeCN (4 mL) and water (0.15 mL). NHS (90 mg, 0.78 mmol) and DMAP (10 mg, 0.08 mmol) were dissolved in MeCN (0.5 mL). mPEG$_{2000}$-OH (156 mg, 0.08 mmol) was dissolved in MeCN (1 mL) with mild heating. DTX (157 mg, 0.19 mmol) was dissolved in MeCN (4 mL) and DMF (0.25 mL). The EDC HCL, NHS, and DMAP reagents were added to the CMC-Ac solution, followed by addition of the Cy5.5-PEG reaction solution and the mPEG-OH and the DTX (Scheme 1B). The solution was stirred overnight at room temperature with protection from light. The product (Cy5.5 Cellax) was purified by the same procedure used to purify Cellax. $^1$H NMR analysis (CDCl$_3$) was conducted to confirm the presence of DTX and PEG, and to estimate molecular composition.

Preparation of SPIONS

Superparamagnetic iron oxide nanoparticles (SPIONs) were prepared according to the method published by Sun.[73] Iron(III) acetylacetonate (353 mg, 1 mmol) was mixed with 1,2-hexadecanediol (1292 mg, 5 mmol), oleic acid (1224 mg, 4.3 mmol), oleic amine (1214 mg, 4.5 mmol) and diphenylether (10 mL) in a 37° C. water bath, and stirred under nitrogen. The vial was heated to 200° C. on a heating block, with occasional mixing. The reaction mixture was cooled to room temperature, the nitrogen atmosphere was flushed, and the solution was heated to 265° C., and refluxed for 30 minutes under nitrogen protection. The solution was cooled to room temperature. Isopropanol (20 mL) was added to the reaction system, and the particles were recovered by centrifugation (2500 rpm, 5 min). Hexane (1 mL) was added to dissolve the compound, and the solution was centrifuged at 2500 rpm for 5 minutes. The supernatant was collected (precipitates discarded) and the solvent was evaporated off. The process (from IPA addition to hexane resuspension) was repeated three times. The SPIONs were dried, weighed, and hexane was added to bring the concentration up to 10 mg/mL.

Assays for DTX Content in Cellax

The DTX content in the Cellax polymer was estimated by HPLC analysis of hydrolyzed polymer samples: Cellax (2 mg) was dissolved in acetonitrile (1 mL) and treated with 8.5% ortho-phosphoric acid (0.3 mL) for 30 seconds on a vortexer. Samples were immediately extracted with ethyl acetate (3 mL). Water was added to each sample (3 mL) in a 15 mL conical tube, and the tube was centrifuged for 5 minutes at 3000 rpm to separate the organic and aqueous layers. The ethyl acetate fraction was isolated, dried by rotary evaporation, and acetonitrile (0.5 mL) was added to dissolve the sample for HPLC analysis.

Cellax Particle Preparation

Cellax (250 mg) was dissolved in acetonitrile (25 mL) without heating. Particles were prepared in batches: 0.2 mL Cellax solution was added dropwise to a vortexing solution of 1.9 mL 0.9% NaCl solution in a 15 mL conical tube. Vortexing was maintained for 1 minute after solution addition. The resulting particle solutions were combined and transferred to a Slide-a-lyzer 10 000 MWCO cartridge, and dialyzed against 0.9% NaCl for three hours, with two exchanges of dialysate. The particles were filtered through a 0.22 um 25 mm Millipore PVDF filter, and transferred to a Vivaspin centrifugal filter unit (25 mL, 10 000 MWCO), and spun at 3000 rpm for 1 hour to concentrate the particles to a 1 mL volume. The size of the particles was determined by dynamic light scattering with a particle analyzer (Zetasizer Nano-ZS, Malvern Instruments Ltd, Malvern, UK). DTX content of the conjugates was determined by diluting the sample 20× in 90/10 saline/DMSO, measuring UV absorbance at 274 nm (Nanodrop, ThermoScientific) and calculating DTX concentration using a DTX calibration curve.

Particles of Cy5.5-Cellax and Cellax (mixed composition) were prepared for in vivo studies, and the particle preparation was optimized by testing a range of ratios. Cellax (100 uL, 10 mg/mL in acetonitrile) was combined with Cy5.5 Cellax (2, 5, 10, 15 and 30 uL, 10 mg/mL in acetonitrile) to form 1, 5, 10, and 15 and 30 wt % Cy5.5 solutions. Each solution was precipitated into 0.9% saline (0.9 mL), filtered through a 0.22 um 25 mm Millipore PVDF filter, and particle size was measured by a Zetasizer.

Particles of Cellax containing SPIONs using Cellax polymer and the SPION solution described above. Briefly, Aliquots of the SPION solution (5, 10, 20, 40 and 100 uL) were transferred to vials, the hexane was dried off. Cellax (10 mg) was dissolved in THF (1 mL), and 100 uL aliquots were added to each SPION vial, and the solutions were well mixed. The SPION/Cellax solutions were then added dropwise to vigorously stirred 0.9% saline (0.9 mL), and these solutions were filtered through 0.22 uM PVDF filters to remove aggregates. Solutions were measured for particle size (Zetasizer) and the absorbance at 500 nm was taken to estimate when SPION incorporation leveled off. Selected samples of Cellax-SPION were analyzed by ICP-OES for iron content: samples were combined 1:1 with 70% nitric acid for overnight digestion, and were then diluted 10× with deionized water prior to analysis.

Determination of Critical Micelle Concentration

The method for determination of the critical micelle concentration was adapted from Zhang, and consists of a fluorescence-based analysis.[67, 74] 1,6-diphenyl-1,3,5-hextriene (DPH, 1.175 mg) was dissolved in acetonitrile (10 mL) to form a stock solution. Cellax (10 mg) was dissolved in 1 mL of the DPH stock solution to form a 10 mg/mL solution, and was serially diluted with the DPH solution to form a series of 10 concentrations of Cellax in a constant concentration of DPH. 100 μL volumes of each sample were precipitated dropwise in 900 uL 0.9% NaCl on a vortexer for 1 minute. 50 μL of each particle solution were transferred to a black 96 well microplate, and fluorescence was measured (Ex 360, Em 460) on a Chameleon plate reader. Two distinct linear curves on a fluorescence vs log concentration plot converge, and the critical micelle concentration was calculated by using linear algebraic solution for intersection of curves.

In Vitro Release of DTX from the Cellax Nanoparticles

Cellax particles were assayed for DTX content, the solution was adjusted to 500 ug DTX/mL, and was sterile filtered through Millipore PVDF 0.22 μm filters. A paclitaxel internal standard was added (5 ug PTX/mL) to the particle solution. Equal volumes of particle solution and fetal bovine serum (FBS) were combined under aseptic conditions, and incubated at 37° C. At selected timepoints (1, 2, 3, 4, 7 and 14 days) 1 mL volumes were taken and combined with 3 mL ethyl acetate, the samples were mixed well for 30 minutes, and then centrifuged at 4000 rpm for 5 minutes to separate the layers. 2.5 mL of the ethyl acetate layer was taken off, the solvent was rotoevaporated, and resuspended in 0.5 mL acetonitrile, and analyzed by HPLC. DTX and PTX peaks appeared at 7.8 min and 8.1 min respectively. A calibration curve for DTX was prepared by spiking a saline/FBS solution with DTX and the PTX internal standard, followed by the same extraction protocol, and this calibration was used to calculate the DTX content in the incubated samples. A new peak appeared in the analysis of incubated samples at 8.4 min, and by LC/MS analysis was determined to be an isomer of DTX (ES+878 mass). The isomer was quantified in a manner similar to DTX.

In Vitro Analysis of DTX Toxicity (IC50 Analysis)

EMT-6 murine mammary carcinoma cells and LL/2 murine Lewis lung cell carcinoma cells were cultured in DMEM media (Invitrogen) with high glucose, supplemented with 10% FBS (Invitrogen), penicillin (100 U/ml) and streptomycin (100 μg/ml) (Invitrogen). The mouse mammary carcinoma cell line EMT-6 was a generous gift from Dr. David Stojdl at the CHEO Research Institute and Dr. Douglas Mahoney at the University of Ottawa. For plating, cells were released from the culture flask with trypsin (Invitrogen), resuspended at a concentration of $1 \times 10^5$ cell/mL, and 100 uL of cell suspension was added to the wells of 96 well polystyrene plate. The cells were maintained for 24 hours in culture (37° C., 5% CO2, humidified) before addition of particles. DTX solutions were made up in DMSO and diluted with media to form a 100 nM stock solution with 0.1% DMSO content. These DTX samples were 2× serially diluted with 0.1% DMSO media. Cellax particles were assayed for DTX content, and 10× serially diluted with media. The cultures were maintained for three days, at which time cell viability was assayed by the XTT assay. Briefly, a 1 mg/mL solution of XTT reagent (Sigma) in water was prepared, and phenazine (Sigma) was added just before analysis (x mg/mL). The culture plates were incubated for two hours at 37° C., and absorbance of each well at 480 nm was then read. Wells treated with media (or 0.1% DMSO media) represent 100% viable cultures, and wells containing no cells represent background signal. In a parallel experiment, the DTX or Cellax-containing media were added to the EMT-6 and LL/2 cultures in four steps, with addition of ¼ the dose every 12 hours for two days. The data was analyzed in GraphPad Prism, and the IC50 for each system was calculated.

Animal Studies

Female BALB/c and C57/BL6 mice (aged 6 weeks, 18-20 g) were purchased from The Jackson Laboratory (Bar Harbor, Me.). All experimental protocols in this study were approved by the Animal Care Committee of the University Health Network (Toronto, Ontario, Canada) in accordance with the policies established in the Guide to the Care and Use of Experimental Animals prepared by the Canadian Council of Animal Care. For each study, the DTX was formulated in a Tween80/ethanol/saline (20:13:67) solution (4 mg DTX/mL), and sterile filtered. The Cellax particles were adjusted to 4, 7.5 or 15 mg DTX/mL in saline and sterile filtered.

Histology and Immunohistochemistry

Tissues from mice (organs, bones, and tumors) were rinsed with saline and fixed in 10% formalin for 2 days, followed by storage in 70% ethanol. Preparation of tissues into slides was performed at the Toronto General Hospital Pathology Research Program lab (Toronto, ON). Ki67 (SP6) antibody (ThermoFisher) was used at a 1/1000 dilution in citrate for 1 hour. CD31 (PECAM) antibody (Santa Cruz) was used at 1/2000 dilution in Tris-EDTA buffer, pH 9 for 1 hour. TUNEL staining was performed according to the method of Wijsman[75]. Prepared slides were analyzed on an Aperio Scanner at the Advanced Optical Microscopy Facility (AOMF) at the Princess Margaret Hospital (Toronto, ON). Image analysis was performed with the ImageScope software accompanying the Aperio scanner. For H&E samples, hemotoxylin and eosin positive pixels were identified with the ImageScope Color Deconvolution V9 algorithm. For TUNEL, Ki67, and CD31 stained samples, brown pixels were counted with the ImageScope Positive Pixel Count algorithm. For each tumor or organ analyzed, three tissue sections were each divided into three equal regions, generating n=9 data points. Image analysis output were positive pixel counts divided by the area analyzed.

Maximum Tolerated Dose (MTD) Study

Healthy BALB/c mice were treated with free DTX at 20 and 40 mg/kg doses, by 200 uL i.v. tail vein injection. Likewise, healthy BALB/c mice were treated with Cellax at 20, 40, 85, and 170 mg/kg DTX equivalent doses. Control mice received injections of Tween80/ethanol/saline or saline. Body weight was monitored for 7 days, and upon sacrifice, organs were harvested for histological and immunohistochemical analysis. Blood was collected, and serum and whole blood were analyzed for serological and hematological parameters, referenced against control blood samples.

Subcutaneous (s.c) Flank Tumor Study in Mice

EMT-6 cells were cultured as described previously. Prior to inoculation, the cells were lifted from the culture plates with TrypLE Express, and re-suspended in supplement free (no FBS, no antibiotics) DMEM media. The EMT-6 cells ($2\times10^5$ cells/50 µl medium) were s.c. inoculated into the shaved right lateral flank of BALB/c mice. After 7 days, when the tumors became palpable, the mice received 40 mg/kg doses of DTX and Cellax, as described in the MTD study. Control animals received saline injections. Each group (DTX, Cellax, and control) was comprised of six mice. The tumor size was measured by a caliper, and body weight was monitored. After 14 days the mice were sacrificed by cervical dislocation, and the heart, lung, liver, kidneys, and tumor were collected for tissue sectioning and staining with H&E, TUNEL, Ki67, and CD31. A second study (similar to the EMT-6 study) was performed with LL/2 cells s.c. inoculated into C57/BL6 mice: the LL/2 cells were suspended in supplement free DMEM media.

Metastatic Tumor Study

Healthy BALB/c mice received an i.v. dose of EMT-6 cells (in supplement free DMEM media) via tail vein injection (50 uL, $2.5\times10^5$ cell/mL), and one day following received a dose of Cellax (40 mg DTX/kg), 40 mg/kg DTX, or saline (n=10/group). A second dose (20 mg/kg DTX) was administered on day 7 post-cell injection. Mice were sacrificed when >20% body weight loss was recorded, or at the first signs of behavioral or mobility dysfunction. The lungs, heart, liver, kidneys, spleen, femurs, and brain were harvested for histological analysis. A Kaplan Meier plot of survival probability was generated from the survival data.

Intraperitoneal (i.p.) Tumor Model Study

PAN02 cells (murine pancreatic cancer) were cultured in RPMI 1640 supplemented with 10% FBS (Invitrogen), penicillin (100 U/ml) and streptomycin (100 µg/ml) (Invitrogen), and pyruvate (1 mM). Prior to inoculation, the cells were lifted from the culture plates with TrypLE Express (Invitrogen), and re-suspended in supplement free (no FBS, no antibiotics) RPMI media. The PAN02 cells ($5\times10^6$ cells/mL, 0.5 mL) were injected into the intraperitoneal space of C57/BL6 mice. One day post-administration of the cells, the mice (n=3 per group) were treated with DTX (40 mg/kg), Cellax (40 mg DTX eqv/kg), or saline. Mice were sacrificed when >20% body weight loss was recorded, or at the first signs of behavioral or mobility dysfunction.

MRI Analysis

MRI monitoring of Cellax-SPION distribution within tumors was performed using a 7T micro-MRI (BioSpec 70/30 USR, Bruker Biospin, Ettlingen, Germany) located at the STTARR facility (Radiation Medicine Program, University of Toronto, Ontario, Canada). Data collection was gated to respiration, and 8-12 slices were collected per tumor imaging session. Images corresponding to a TE=10 ms were processed in MIPAV software. Briefly, tumor volumes were delineated with polygons throughout the 8-12 slices through the tumor volume to define a volume of interest (VOI). Sections of adjacent muscle tissue were likewise delineated with a VOI. Hypointense tumor voxels were defined as tumor voxel intensity minus 5× the standard deviation of mean muscle voxel intensity. By performing a thresholding operation on each tumor VOI excluding voxels above the 5× SD limit, a hypointense volume was calculated. The volume fraction of each tumor containing hypointense voxels was calculated as non-threshold volume/threshold volume.

Camptothecin Analogue

Acetylated carboxymethylcellulose (CMC-Ac, 75 mg, 0.29 mmol acid) was weighed into a 25 mL glass flask, and dissolved in anhydrous DMF (1 mL) under nitrogen protection. Camptothecin (CMT, 50.0 mg, 0.15 mmol) was weighed into a 25 mL glass vial, and dissolved in anhydrous DMF (15 mL) with mild heating. The CMT solution was added to the reactor, and the solution was chilled to 0° C. PyBOP (137 mg, 0.26 mmol), DMAP (64 mg, 0.53 mmol), and mPEG-OH (175 mg, 0.09 mmol) were weighed into glass vials, dissolved in anhydrous DMF (1 mL each), and added to the reactor. DIPEA (38 µL, 0.22 mmol) was added to the reactor by syringe. The reaction was raised to room temperature after 1 h, and left to stir overnight under nitrogen protection. The reaction solution was concentrated by rotary evaporation, chilled with an ice bath, and 10% NaCl (25 mL) was added.

The solution was then acidified to pH 2.5 by addition of 0.1N HCl. The suspension was stirred for 1 hour at room temperature, the solids were recovered by centrifugation, washed four times with water, and dried overnight. The solid material was dissolved in DMF (2 mL), and dialyzed against methanol for three hours to extract un-reacted CMT. The particle suspension was evaporated to dryness, and re-suspended as a 1 mg/mL solution in DMF. 1H NMR (CDCl$_3$) δ: 7.29-8.51 (5H, CMT), 7.28 (1H, CMT), 5.76 (2H, CMT), 5.32 (2H, CMT), 3.0-5.5 (m, CMC polymer), 3.658 (PEG), 1.027 (3H, CMT). Particles are prepared by precipitation into 10× volume of 0.9% saline.

Paclitaxel (PTX) Analogue

Acetylated carboxymethylcellulose (CMC-Ac, 50 mg, 0.19 mmol acid) was weighed into a 25 mL glass vial, and dissolved in MeCN (0.5 mL). EDC HCl (112 mg, 0.58 mmol) was dissolved in MeCN (3 mL) and water (0.1 mL). NHS (67 mg, 0.58 mmol) and DMAP (24 mg, 0.19 mmol) were dissolved in MeCN (1 mL). mPEG-OH (117 mg, 0.06 mmol) was dissolved in MeCN (1 mL) with mild heating. PTX (67 mg, 0.08 mmol) was dissolved in MeCN (2 mL) and DMF (0.2 mL). The EDC HCL, NHS, and DMAP reagents were added to the CMC-Ac solution, followed by addition of the mPEG-OH and the PTX. Reaction purification was identical to that of the DTX conjugate. Composition was confirmed by H NMR (41 weight % PTX, 5.7 wt % PEG). Particles were isolated with a size of 115 nm and a PDI of 0.1.

Doxorubicin (DOX) Analogue

Acetylated carboxymethylcellulose (CMC-Ac, 100 mg, 0.38 mmol acid) was weighed into a 25 mL glass vial, and dissolved in DMF (4 mL). DCC (158 mg, 0.76 mmol) and DMAP (9 mg, 0.08 mmol) were dissolved in DMF (0.5 mL). mPEG-OH (574 mg, 0.11 mmol) was dissolved in DMF (1 mL). DOX (83 mg, 0.15 mmol) was dissolved in DMF (0.25 mL). The DCC and DMAP reagents were added to the CMC-Ac solution, followed by addition of the mPEG-OH and the DOX. After reaction overnight, the reaction solution was combined with 4 mL water, and dialyzed against water to extract uncoupled DOX. The solution was dried, resuspended in DMF, and precipitated through ether: the polymer in the ether solution was recovered by rotary evaporation. In NMR, most DOX signals are overlapped with polymer, but the product is dark red. 1H NMR (DMSO) δ: 7.1-7.8 (m, Ar H, DOX), 5.1 (dd, 1H, DOX), 3.63 (s, 4H, PEG), 3.32 (s, 3H, PEG), 3.0-5.5 (m, CMC polymer), 1.96 (m, 3H, acetyl), 1.25 (d, DOX). The CMC-PEG-DOX product was dissolved in DMSO and precipitated into saline: no discrete particle population formed, suggesting that self-assembly was impeded with a relatively hydrophilic drug such as DOX.

PEG5000 Analogue of Cellax

Acetylated carboxymethylcellulose (CMC-Ac, 100 mg, 0.38 mmol acid) was weighed into a 25 mL glass vial, and dissolved in MeCN (1 mL). EDC HCl (147 mg, 0.76 mmol) was dissolved in MeCN (4 mL) and water (0.2 mL). NHS (88 mg, 0.76 mmol) was dissolved in MeCN (1 mL). mPEG-OH 5000 (574 mg, 0.11 mmol) was dissolved in MeCN (2 mL) with mild heating. DTX (216 mg, 0.27 mmol) was dissolved in MeCN (4 mL). The EDC and NHS reagents were added to the CMC-Ac solution, followed by addition of the mPEG-OH and the DTX. Purification of the product was identical to that of Cellax synthesized with mPEG-OH 2000. 1H NMR (CDCl$_3$) δ: 8.03 (d, 2H, C25 and C29), 7.62 (t, 1H, C27), 7.49 (t, 2H, C26 and C28), 7.41 (m, 4H, C31, C32, C34, C35), 7.38 (m, 1H, C33), 6.23 (m, 1H, C13), 5.70 (m, 1H, C2), 5.25 (m, 1H, C4'), 5.08 (br, 1H, C10), 4.79 (d, 1H, C5), 4.37 (m, 1H, C20-A), 3.62 (s, 4H, PEG), 3.0-5.5 (m, CMC polymer), 1.99 (m, 3H, acetyl), 1.29 (s, 3H, C16). Particles were prepared by precipitation of an MeCN solution, as previously described: 119 nm, PDI=0.3.

Lower MW CMC Analogue

Sodium carboxymethylcellulose (CEKOL 4K, 10 g) was acetylated following the same method applied to the Cekol 30K material. Acetylated carboxymethylcellulose (CMC-Ac, 100 mg, 0.39 mmol acid) was weighed into a 25 mL glass vial, and was dissolved in MeCN (1 mL). EDC HCl (149 mg, 0.78 mmol) was dissolved in MeCN (4 mL) and water (0.2 mL). NHS (90 mg, 0.78 mmol) and DMAP (10 mg, 0.08 mmol) were dissolved in MeCN (0.25 mL). mPEG-OH (234 mg, 0.12 mmol) was dissolved in MeCN (1 mL) with mild heating. DTX (157 mg, 0.19 mmol) was dissolved in MeCN (4 mL) and DMF (0.3 mL). The EDC HCL, NHS, and DMAP reagents were added to the CMC-Ac solution, followed by addition of the mPEG-OH and the DTX. Purification of the product is identical to that described for process described for the CEKOL 30K CMC-Ac analogue. Particles were isolated from this preparation with a size of 140 nm.

TEM Analysis of the Cellax Particle

Cellax particles were diluted 100× in deionized water, and a 2 μL aliquot of solution was pipetted onto the surface of formvar coated copper TEM grids (TedPella, Redding, Calif.) and allowed to air dry. Analysis was performed on an Hitachi HD-2000 STEM at the Centre for Nanostructure Imaging (Department of Chemistry, University of Toronto), using a high angle annular dark field detector, with an activation voltage of 200 kV and a current of 10 mA. TEM analysis of the particles supports the Zetasizer measurement (104+/−15 nm), and as seen in Figure Example 6, the particles are spherical.

Incorporation of CMT into a Cellax Particle

Cellax (3 mg) was dissolved in THF (0.27 mL), and 30 uL of a 1.0 mg/mL solution of camptothecin (CMT) in DMSO was added. The CMT/Cellax solution was then added dropwise to vigorously stirred 0.9% saline (2.7 mL), and this solution was filtered through a 0.22 uM PVDF filter to remove any aggregates. Particle size was measured with a Zetasizer: 120 nm, PDI=0.3. The particles were diluted in DMSO (10×), and fluorescence (Ex 325 nm, Em 460 nm) was measured, and a 100% encapsulation efficiency was calculated.

Example 1

Synthesis of Cellax

Acetylation of the Carboxymethylcellulose

Acetylation of the CMC polymer proceeded smoothly, provided that the CMC polymer was scrupulously washed in each stage of the protocol. For example, residual sulphuric acid caused material discoloration and residual water impeded the anhydride reaction. Materials that did not acetylate successfully did not ultimately dissolve in the acetic acid solvent. However, when the washing procedures were suitably intensive and thorough, the reactions were quantitative, as assessed by H NMR analysis. $^1$H NMR (CDCl$_3$) δ: 3.0-5.5 (m, CMC H), 2.02 (m, acetyl CH$_3$).

Conjugation of the PEG and DTX:

CMC-Ac was soluble in DMF, but DTX and PEG coupling reactions performed in DMF did not exhibit good yields, and particles formed from these materials were unstable and non-uniform. In solvent screening, MeCN promoted higher conversions, and subsequently, all conjugation reactions were performed in this solvent. In addition, to minimize the dilution of reagents, 1.5 vol % water was required to dissolve EDC, and 3.0 vol % DMF was required to dissolve the DTX in the MeCN solvent. Purification of the polymer by dialysis was initially attempted, but as PEG, DTX, and the CMC reagents possess different solubility profiles, problems with precipitation and low purification efficiency occurred. Washing the powdery Cellax product with water proved effective in extracting un-reacted PEG, and precipitation through ether effective in extracting un-reacted DTX. Effective extraction of the un-reacted PEG and DTX was confirmed by GPC analysis of the product. However, the CMC polymer absorbed to the polystyrene columns, so GPC analysis was restricted to identification of impurities. $^1$H NMR (CDCl$_3$) δ: 8.12 (d, 2H, C25 and C29), 7.61 (t, 1H, C27), 7.51 (t, 2H, C26 and C28), 7.41 (m, 4H, C31, C32, C34, C35), 7.34 (m, 1H, C33), 6.23 (m, 1H, C13), 5.71 (m, 1H, C2), 5.25 (m, 1H, C4'), 5.10 (br, 1H, C10), 4.98 (d, 1H, C5), 4.32 (m, 1H, C20-A), 4.25 (m, 1H, C7), 4.19 (br, 1H, C20-B), 3.64 (s, 4H, PEG), 3.38 (s, 3H, PEG), 3.0-5.5 (m, CMC polymer), 2.57 (m, 1H, C6-A), 2.38 (3H, C22), 2.02 (m, 3H, acetyl), 1.86 (m, 4H, C6 and C18), 1.75 (br, 3H, C19), 1.34 (s, 9H, C7', C8', C9'), 1.29 (s, 3H, C16), 1.14 (s, 3H, C17). See FIG. 2A for the spectra described, and FIG. 2B for the DTX carbon numbering scheme. The relative mol % of each unit (CMC, PEG, and DTX) in the conjugate was estimated by integration of the spectra, and by back-calculation using the molecular weight of each component, weight percentages were calculated (Table 1). DTX content in the Cellax was further estimated by HPLC analysis of DTX hydrolyzed from the conjugate using treatment with orthophosphoric acid, and this analysis confirmed the 30 wt % DTX composition.

Compositions bracketing the functional Cellax formulation were prepared by varying both PEG and DTX. By $^1$H NMR analysis, the peak assignments reported above for Cellax were identical (data not shown), but the integrations of the DTX peaks varied. As shown in Table 2, the DS for DTX in functional compositions ranged from 13.4-26.4 mol % (22.5-43.3 wt %), and the DS for PEG ranged from 0.9-5.4 mol % (3.5-22.7 wt %). The preferred composition contained 15.1-23.7 mol % DTX and 1-1.1 mol % PEG, and the further preferred composition contained 20.5 mol % DTX and 1 mol % PEG. Within a defined range of composition particle forming properties were established, and clear delineation of the boundaries was established where defined nanoparticles could no longer be measured.

TABLE 1

Composition analysis of the Cellax by $^1$H NMR and HPLC analysis

| Component | MW (g/mol) | DS$^a$ | Wt %$^a$ | Wt %$^b$ |
|---|---|---|---|---|
| DTX | 807.8 | 20.5 +/− 2.0 | 36.9 +/− 2.6 | 30 |
| PEG | 2000 | 1.0 +/− 0.3 | 4.7 +/− 1.5 | — |

$^a$Estimated by H NMR from 8 batches
$^b$Estimated by hydrolysis and HPLC analysis.

TABLE 2

Composition comparison between batches of Cellax conjugates prepared with differing molar composition.

| | | | | |
|---|---|---|---|---|
| 20 | 100 | 13.4 | 5.4 | 49.4 |
| 20 | 75 | 13.8 | 4.8 | 71.8 |
| 50 | 100 | 24.5 | 2.7 | 100.2 |
| 50 | 150 | 23.7 | 3.6 | 102.1 |
| 30 | 30 | 15.1 | 1.1 | 105.4 |
| 50 | 70 | 23.6 | 2.1 | 107.2 |
| 20 | 30 | 12.9 | 2.0 | 108.4 |
| 20 | 50 | 13.1 | 3.6 | 116 |
| 50 | 50 | 23.7 | 1.6 | 117.8 |
| 40 | 30 | 20.5 | 1.0 | 118.2 |
| 50 | 30 | 16.3 | 2.6 | 118.4 |
| 50 | 20 | 26.4 | 0.9 | 141.9 |
| 10 | 30 | 8.8 | 1.8 | 278.1 |
| 50 | 10 | 27.3 | 0.4 | n.a. |
| 90 | 30 | 36.6 | 2.1 | n.a. |
| 20 | 20 | 12.3 | 1.6 | n.a. |
| 20 | 150 | 11.3 | 7.4 | n.a. |
| 50 | 200 | 27.4 | 4.9 | n.a. |

N.a. indicates that defined particles could not be detected.

The synthesis of the Cy5.5-Cellax polymer mirrored that of the Cellax polymer, excepting that Cy5.5-PEG was incorporated into the reaction scheme. By $^1$H NMR, the spectrum described above was detected, but Cy5.5 peaks could not be readily detected due to spectral overlap and low signal compared to the balance of polymer components. However, the Cy5.5-Cellax product was dark blue and its fluorescence in the near-IR was confirmation of Cy5.5 incorporation. The Cy5.5-Cellax particles, when dialyzed with 10K MWCO cartridges, or when concentrated with Vivaspin 10K filter did not leak blue dye, confirming the Cy5.5 content was stably incorporated.

Example 2

Cellax Particle Formulation, In Vitro DTX Release, and Animal Studies

A series of tests were conducted using different methods of particle preparation, including solvent exchange by dialysis against aqueous solution, thin film hydration, and precipitation. Good results were achieved using aqueous precipitation, but the other common particle-forming techniques did not produce defined particles. As described in Table 2, the aqueous system used to prepare the particles had an impact on particle dimension and stability. For example, particles prepared in phosphate buffer saline (25 mM PBS) were initially 134 nm in size but over the course of a few hours, these particles visibly aggregated. Conversely, particles prepared in 10% sucrose or 0.9% saline ranged from 120-130 nm, and remained stable in 4° C. storage for at least one month (limit of testing to date). As well, the Cellax particles prepared in saline and incubated with FBS did not change in dimension. The critical micelle concentration, determined by the DPH assay, was 0.1 mg/mL.

TABLE 2

Cellax particle characteristics in different aqueous systems

| Solution | Size (nm) | PDI |
|---|---|---|
| PBS | 134.0 +/− 3.4 | 0.1 +/− 0.08 |
| Saline (0.9%) | 125.1 +/− 2.5 | 0.05 +/− 0.01 |
| Sucrose (10%) | 128.5 +/− 3.2 | 0.10 +/− 0.04 |

Cy5.5-Cellax particles were prepared in a protocol similar to that applied to Cellax particles, except that 1, 5, 10, 15 and 30 wt % of these particles were Cy5.5-Cellax, with the balance made up as Cellax. The particle size measurements were stable at 102-100 nm up to 15 wt % Cy5.5-Cellax, after which the measurements became erratic, possibly due to fluorescence effects in the Zetasizer instrument.

Cellax-SPION particles were prepared by precipitating a THF solution of SPION and Cellax into saline, followed by dialysis and filtration through 0.22 μm filters. A series of SPION:Cellax ratios were tested (9-50% SPION by weight): integration of SPION leveled off at 30 wt %, with an integration efficiency of 77% and a final post-filtration SPION content of 25.4+/−2.5 wt %. The size of Cellax-SPION particles was 115.4 nm with a PDI of 0.104, and was readily sterilized through 0.22 μm filters. The Cellax-SPION particles were concentrated by Vivaspin filtration to yield a 11.4 mg/mL SPION, 12 mg/mL DTX, 40 mg/mL Cellax particle solution. MR analysis confirmed that Cellax-SPION particles could provide negative contrast in T1 and T2 modes: as depicted in FIG. 3A, as the solution of particles were diluted from 168 ug SPION/mL downwards, the T1 contrast likewise diminished in a linear relationship. More importantly, the T2 contrast of the SPION particles was high, and when the Cellax-SPIONS were injected into a mouse (20 mg/kg SPION, 133 mg/kg DTX), excellent contrast in the tumor was detected by T2 and T2* imaging. The EMT-6 tumor mass could be seen in the background imaging series (FIGS. 3B and 3C), and 3 hours post-injection (FIGS. 3D and 3E), the T2 and T2* images shows clear accumulation of SPION. After 24 and 72 hours, these particles remain in residence, moving within the tumor. Image analysis was performed by first defining the tumor volume (VOI). Following that analysis, a threshold intensity defining hypointense voxels was established: the mean intensity and standard deviation (SD) of neighboring muscle VOI's was measured, and multiples of SD were subtracted from the mean intensity until no voxels were counted (5SDs). For all tumor images, the 5SD value of the reference muscle VOI was subtracted from the un-thresholded tumor volume to generate the hypointense volume. As seen in FIG. 3F, the hypointense volume fraction increased rapidly at 3 hours (25%), and peaking at 24 hours in both T2 and T2* images at 30%. At 72 hours, the hypointense volume fraction decreased to 15%.

The Cellax particles were suspended in a 50:50 mixture of FBS, and DTX release from the particles was monitored over the course of three weeks. In the preliminary study, the FBS was heat-deactivated, and very little DTX release could be detected (data not shown). In the subsequent study with non-denatured FBS, an additional peak was detected in the HPLC analysis, and when the analysis mirrored on a HPLC/MS system, both the DTX peak and the new peak were detected as 808 Da in MS+ mode, indicating that DTX was isomerizing to 7-epidocetaxel. Subsequently, both DTX and 7-epidocetaxol were quantitated, and the combined quantity of DTX and the isomer summed to express total taxanes. As shown in FIG. 4, the release of taxanes over the course of three weeks was controlled, reaching full release at 21 days. Approximately half of the conjugated DTX was released as active DTX.

The in vitro IC50 analysis of the Cellax confirmed a cytotoxic effect against both EMT-6 mammary carcinoma and LL/2 lung carcinoma cell lines (Table 3 and FIG. 5A-B). The control CMC-PEG polymer mass concentration in cell culture was matched to the mass concentrations of Cellax, and at no level were there any indications of cytotoxic effects on these cells. The EMT-6 cells are more sensitive to the effects of a bolus dose of DTX, exhibiting an IC50 of 80 nM, compared to 767 nM for the LL/2 cells. However, both the EMT-6 and the LL/2 cell populations were more influenced by the Cellax particle treatment, with IC50's of 9 and 19 nM, respectively. EMT-6 and LL/2 cultures were also treated with repeated doses of DTX (20 and 200 mM respectively, four applications over two days), to determine if one-doses or metronomic doses of DTX would lead to differing results. Indeed, the viability of EMT-6 and LL/2 cultures were 20 and 12% respectively compared to controls (compared to 50% with a single dose), indicating that sustained exposure to DTX has a more anti-viability effect on these cells.

TABLE 3

In vitro cytotoxicity analysis (IC50 analysis)

| Cell line | IC50 DTX (nM) | IC50 DTX (nM) Metronomic | IC50 Cellax (nM) |
|---|---|---|---|
| EMT-6 (mammary) | 80 +/− 3 | 6 +/− 2.6 | 9 +/− 3 |
| LL/2 (lung) | 767 +/− 10 | 12 +/− 4 | 19 +/− 3 |

In the MTD study, the BALB/c mice demonstrated body minor weight loss on administration of the Tween80/ethanol/saline solutions (FIG. 6A). Mice treated at 20 mg/kg DTX did not gain or lose weight, but mice at the 40 mg/kg dosing exhibited slightly depressed body weight and mild piloerection. Conversely, mice treated with the Cellax particles at 20, 40, 85 and 170 mg/kg DTX dosing did not exhibit signs of physical stress, and only the 170 mg/kg Cellax dosing group exhibited weight loss (FIG. 6B). The mice in the 170 mg/kg treatment group regained their original body weight within one week of dose administration (FIG. 6B). Hematology and blood chemistry analysis did not reveal any abnormalities (Table 4). Histology, and immunohistochemical analysis of the 170 mg/kg mouse organs also did not reveal any abnormalities.

TABLE 4

Serological and hematological analysis of blood from Balb/c mice treated with Cellax (170 mg DTX/kg).

| Serological Parameter | Units | Control | Cellax |
|---|---|---|---|
| Total Protein | g/L | 50 +/− 9 | 54 +/− 3 |
| Albumin | g/L | 36 +/− 4 | 39 +/− 2 |
| Globulin | g/L | 14 +/− 5 | 16 +/− 1 |
| A/G Ratio | | 3 +/− 1 | 3 +/− 0 |
| Bilirubin | umol/L | 1.5 +/− 0.5 | 2 +/− 0.4 |
| ALP | IU/L | 134 +/− 33 | 158 +/− 9 |
| ALT | IU/L | 73 +/− 53 | 56 +/− 4 |
| AST | IU/L | 267 +/− 218 | 252 +/− 74 |
| Urea | mmol/L | 9 +/− 2 | 9 +/− 1 |
| Creatinine | umol/L | 13 +/− 1 | 19 +/− 3 |

| Hematology Parameters | Description | Control | Cellax |
|---|---|---|---|
| RBC ($\times 10^{12}$/L) | Red blood cells | 9 +/− 3 | 11.8 +/− 0.03 |
| Hgb (g/L) | Hemoglobin | 140 +/− 28.3 | 161 +/− 0 |
| HCT (L/L) | Hematocrit | 0.5 +/− 0.1 | 0.63 +/− 0.01 |
| MCV (fL) | Mean corpuscular volume | 57.9 +/− 6.9 | 52.9 +/− 0.49 |
| MCH (pg/cell) | Mean corpuscular hemoglobin | 15.9 +/− 2.4 | 13.6 +/− 0 |
| MCHC (g/L) | Mean corpuscular hemoglobin concentration | 275.5 +/− 9.2 | 257 +/− 2.8 |
| PLT ($\times 10^9$/L) | Platelets | 776 +/− 343.7 | 629.5 +/− 55.6 |
| WBC ($\times 10^9$/L) | White blood cells | 5.5 +/− 4.8 | 8.2 +/− 0.8 |
| MPV (fL) | Mean platelet volume | 5.7 +/− 1.5 | 4.6 +/− 0.1 |
| RDW% | Red blood cell distribution | 18 +/− 0 | 19.3 +/− 0.1 |

TABLE 4-continued

Serological and hematological analysis of blood from Balb/c mice treated with Cellax (170 mg DTX/kg).

| | | | |
|---|---|---|---|
| NE (×10⁹/L) | Neutrophils | 1 +/− 0.5 | 1.2 +/− 0.2 |
| LY (×10⁹/L) | Lymphocytes | 4.2 +/− 4.2 | 6.6 +/− 0.4 |
| MO (×10⁹/L) | Monocytes | 0.3 +/− 0.1 | 0.3 +/− 0.1 |
| BA (×10⁹/L) | Basophils | 0 +/− 0 | 0.01 +/− 0.01 |
| EO (×10⁹/L) | Eosinophils | 0.1 +/− 0 | 0.03 +/− 0.02 |

In pilot efficacy studies, mice were inoculated with the EMT-6 and LL/2 cells to generate syngeneic tumor models, and these mice were treated a single matched dose of 40 mg/kg DTX or 40 mg eqv/kg Cellax. In the EMT-6 flank model, the free DTX had a minor (not significant) effect on tumour growth compared to the control saline-treated mice. A single dose of 40 mg/kg Cellax had a significant impact on tumor growth (FIG. 7A). The study was terminated when the control and DTX-treated mice began to exhibit tumor lesions. In the LL/2 flank model, the free DTX did not alter tumor growth characteristics, but 40 mg/kg Cellax had a significant impact on tumor growth, albeit less compared to the EMT-6 (FIG. 7B). When 170 mg/mg Cellax treatment was applied to the LL/2 tumors, an increased benefit was measured (FIG. 7B). Both the EMT-6 and LL/2 tumor models were aggressive, but the LL/2 posed a challenge due to rapid tumor growth and this is reflected in the variation, which was more substantial in the LL/2 group.

In both the EMT-6 and LL/2 models, tumors and organs from sacrificed mice were harvested, fixed, sectioned and stained with H&E, and chromogenic TUNEL, Ki67, and CD31 antibodies. EMT-6 Model: in the H&E stained sections, it was apparent that portions of the Cellax and DTX treated tumors were necrotic (FIG. 8A), and this observation was mirrored in the Ki67 (cell viability), CD31 (angiogenesis) and TUNEL staining (apoptosis). By visual examination, it was evident that DTX caused necrosis/apoptosis, and this effect was more pronounced within the Cellax treated tumors. These histology observations were followed by image analysis to verify the observation with quantitative measurements. As seen in FIG. 9 B-D, Cellax treatment caused significantly more apoptosis, and inhibited cell replication and angiogenesis to a significant extent, both in comparison to DTX treated tumors, and the controls. Analysis of the other organs in the system (also by H&E, TUNEL, Ki67 and CD31) revealed that some damage was occurring in the kidneys and lungs of DTX treated mice, but this could only be detected by the TUNEL staining (FIG. 8B, FIG. 9 E, F). By analysis of the H&E images for example, all the organ tissue morphologies looked normal (data not shown). No damage was detected in the liver, heart or spleen. Analysis of Tween80/ethanol/saline treated mice kidneys and lungs (carrier solution for DTX) did not turn up positive TUNEL staining, indicating that toxicity in the DTX-treated mice was attributable to the drug, not the carrier solution. LL/2 model: the presence of necrotic tissue was only detected in the Cellax treated tumors (FIG. 10A), and positive TUNEL staining was minimal in control and DTX treated tumors (FIG. 10B), whereas increased positive staining in the Cellax treated tumors corresponded to the necrosis observed in FIG. 10A. Analysis of the other organs by H&E and TUNEL did not uncover any physiological abnormalities or apoptosis, suggesting that Cellax at 40 and 170 mg/kg dosing was non-toxic and safe to normal tissues in the C57/BL6 mice.

In the metastatic cancer model in Balb/c mice, on-set of disease symptoms was read through weight changes and behavioral observations, with sacrifice being determined by parameters set by the staff veterinarians within the AUP. Onset of weight loss in control mice (saline injections) was observed on day 5, and was rapid (see FIG. 11A). A similar rapid onset of weight loss on day 6 was observed in DTX treated mice (40 mg/kg), but in the Cellax group, weight loss did not begin until after day 8, and the rate of weight loss in the Cellax group was slower. Additional signs of disease stress included piloerection (all mice in control and DTX groups) and parelsis, especially in leg movements (5/10 for control group, 4/10 for DTX group). The Cellax treated mice did not exhibit piloerection or parelsis at any point, even when weight loss necessitated sacrifice, suggesting some aspect of cancer (such as chord compression) was absent in the Cellax-treated mice. The median survival times of the control, DTX, and Cellax groups was 8, 9, and 15 days respectively (FIG. 11B): Cellax increased survival time 170% compared to DTX, and 187% compared to untreated mice. Histology analysis of the tissue sections indicated that primary disease burden was in the lungs (FIG. 11C), with no detectable tumor mass in the heart, liver, spleen, kidneys, brain or bone marrow. By visual inspection, the disease burden in the Cellax treated mice was less compared to the control and DTX mice.

In the PAN02 pancreatic cancer model in EMT-6 mice, onset of symptoms become apparent five days post-inoculation, with mice exhibiting weakness, lack of activity, and weight loss. On sacrifice and necropsy, there were varied presentations of cancer: enlarged intestines, tumor nodules located on the intraperitoneal wall and on the intestines, enlarged pancreas, enlarged and dark bile nodules in the liver, swollen stomach, and ascites fluid. The control mice exhibited symptoms first followed by the GEM 120 mg/kg treated mice, and as shown in FIG. 12, decline was rapid once onset of symptoms was detected. Unlike the saline and gemcitabine dosed mice, the DTX and Cellax mice did not exhibit signs of weight loss or disease symptoms.

One objective of this study was to develop a self-assembling carbohydrate-based therapeutic nanoparticle, and to increase the effectiveness and reduce the toxicity of docetaxel. As described in Table 5, the Ringsdorf design parameters[2-3] were supplemented with those required for nanoparticle formation and enhanced PK.[7, 12, 28-30] For effective nanoparticle forming properties, the hydrophobic and hydrophilic elements of the macromolecule were balanced, so that when these amphiphilic structures contacted aqueous solution, they would spontaneously assemble into thermodynamically stable micelles.[52] CMC is generally regarded as safe (GRAS), and finds widespread use in biomaterials,[76] pharmaceutical formulation,[51] and food.[77] Despite CMC' subiquitous presence in formulation, only a small number of groups have examined nanoparticle formulation using CMC, and most polysaccharide nanoparticles are formulated with chitosan, dextran, and heparin derivitives.[52-66, 78]

TABLE 5

Design parameters for a preferred Cellax nanoparticle

| Design Parameter | Composition | Rationale |
|---|---|---|
| Polymer | Carboxymethyl cellulose, | Approved excipient, commercially available, functional groups available for modifications. |
| Solubility | PEG, MW ≈ 2000 | Dual role as stealth chemistry and solubilizing agent. Higher MW PEG |

TABLE 5-continued

Design parameters for a preferred Cellax nanoparticle

| Design Parameter | Composition | Rationale |
| --- | --- | --- |
| Stealth | PEG, MW ≈ 2000 | more difficult to conjugate and purification impeded. Established and effective composition. |
| Drug | Docetaxel | Well characterized chemotherapeutic. Hydrophobic (drives particle self assembly). |
| Cleavable Linker | Ester | Hydrolyzable, slow release model. |
| Targeting | Passive (EPR) | Known and effective method of tumor targeting. |
| Hydrophobic balance | CMC acetylation and DTX | Particle formation favored with DTX, acetylation reduces water solubility of the CMC polymer. |

Sodium CMC is a water soluble polymer composed of repeating anhydroglucose units, and is only sparingly soluble in organic solvents such as DMF or DMSO.[79] In initial synthetic efforts, the sodium counterion on the carboxylic acid was exchanged with triethylamine (TEA) or tetrabutylammonium (TBA)[80] in order to generate solvent soluble CMC. However, conversion of carboxylic acid groups to DTX and PEG esters using EDC/NHS chemistry was low (<10%), and particles formed using these materials were heterogeneous in size and prone to self-aggregation. In the published art, interest in solvent solubility of CMC has been primarily the domain of chemical and polymer coating companies, where compatibility of the CMC with other resins and the dispersion forming properties of this material were optimized by adjusting solvent solubility though chemical modifications. For example, Namikoshi[72] optimized a chemical process for preparation of carboxyalkyl acetyl celluloses, wherein the sodium salt was converted to a free acid, and the hydroxyl groups were acetylated quantitatively in the presence of acetic anhydride and sulphuric acid catalyst in an acetic acid solvent at 40-60° C. Critical to this reaction was the complete dehydration of the free acid prior to acetylation reactions. Subsequent to this modification, the solvent soluble free acid CMC(Ac) could be rendered water soluble by converting the free acid back to a sodium salt. Allen[81] described a similar process for acetylation of the hydroxyl groups, but added sulphuric acid post-acetylation and heated the polymer to partially hydrolyze the acetyl esters and achieve partial water solubility, in order to modulate wetting and gelling properties in coating formulations, and provide for crosslinking site with isocyanates or melamine. Of particular interest in this patent, the inventors noted that subsequent esterification of the carboxyl acid group on each anhydroglucose unit was strongly dependant on the carboxylic acid being a free acid. These reports are confirmed in this work, both in terms of solubility profiles and the reactivity of the carboxylic acid groups.

The degree of substitution (DS) per anhydroglucose unit, as specified by the manufacturer, was 0.8 mol acid per mol anhydroglucose, with 2.2 mol hydroxyl (subsequently converted to acetyl groups). For a CMC(Ac) molecule we were able to calculate the theoretical moles of acetyl group and acid group, and design conjugation schemes accordingly. $^1$H NMR analysis confirmed the DS calculations: by integration of the proton NMR spectra, the ratio of anhydroglucose protons and acetyl protons was found to conform to prediction. To an EDC/NHS activated CMC(Ac) polymer in DMF were fed varying mol % mPEG-OH and varying mol % DTX (relative to the carboxylic acid groups), and by $^1$H NMR analysis these reactions produced a polymer with 0.9-5.4% DS with PEG and 13.4-26.4% DS DTX. By $^1$H NMR estimation and total drug content analysis (UV), the finished Cellax molecule contains 22.5-43.3 wt % DTX and 3.5-22.7 wt % PEG. Variance in the outcome of synthesis was anticipated given the polydispersity of the Cellax polymer, and as more batches were prepared, the purity of the DMF and acetonitrile solvents was identified as an important factor in a positive reaction outcome.

For synthetic amphiphilic macromolecules such as PEG-polycaprolactone, a plurality of particle making approaches is effective.[19-21, 82] Producing well defined and stable Cellax nanoparticles however proved to be more method dependant. For example, Cellax was dissolved in acetonitrile or DMF, and this solution was dialyzed against multiple exchanges of water to remove the solvent: the polymer invariably aggregated into clumps. Thin film methodologies were likewise ineffective at producing well defined nanoparticles. Precipitation of an MeCN or THF solution into aqueous media (10× dilution) proved to be the best approach for forming well defined nanoparticles, provided the concentration of Cellax in the MeCN solution ranged between 10-25 mg/mL. It was observed that particles formed from 25 mg/mL solutions were approximately 150 nm in size, and particles formed from 10 mg/mL solutions were smaller (100 nm). For all subsequent work, the 10 mg/mL and 10× dilution parameters were set so as to provide for the smallest well defined population of nanoparticles. The choice of buffer or aqueous media was likewise important. Particles prepared in PBS were initially of reasonable dimension, but aggregated within hours. Particles prepared in 0.9% sodium chloride, 10% sucrose, or water were stable, and maintained their dimensions when transferred into a 50 vol % solution of FBS.

Prior to in vitro or in vivo analysis, the release of DTX from Cellax nanoparticles was analyzed, to affirm that hydrolysis of the ester bonds would occur in the presence of serum. Samples of particles incubated in FBS were extracted with ethyl acetate, and by LC/MS analysis, two peaks with an ES+ MS value of 808.8 m/z were detected, corresponding to DTX and a DTX isomer, 7-epidocetaxel: these peaks were analyzed to generate a total taxane release value.[70, 83-84] As shown in FIG. 4, the release of DTX over the course of 21 days was sustained, culminating in full release, with half of the total taxane quantity active DTX. This data was contextualized with respect to published reports on taxane conjugates. For example, release of PTX from water soluble carboxylmethyl dextran conjugates is rapid, with total release occurring within 3-4 days.[78] Release of DTX from water-soluble albumin conjugates is rapid, with 40% release in 1 day.[68] Release of DTX from PEG conjugates is rapid, with full release in 6 days.[67] Release of PTX from polyglutamic acid conjugates is comparatively slow, with 15-30% release recorded in 4-5 days.[85-86] In the absence of detailed studies of molecular topography for the water-soluble conjugate examples, it is posited that ready access of hydrolytic enzymes to the ester bonds linking the taxane to the macromolecule drives the high rate of hydrolysis. Cellax (like Polyglumex) is composed of a polymer chain with hydrophobic taxanes conjugated along the length of the molecule: molecular modeling of Polyglumex indicates that interactions between the taxane molecules leads to collapse of the polymer chain to form a particle with a hydrophobic interior and hydrophilic exterior.[87] For Cellax, the condensed state of the polymer and the addition of PEG shielding appears to effectively control hydrolysis, but at a rate greater than that reported for Polyglumex.

In vitro, the activity of released DTX was measured by following cancer cell line viability in the presence of Cellax particles. Both the mammary carcinoma EMT-6 and lung carcinoma LL/2 exhibited sensitivity to free DTX in conformity with published reports[88-89], and significantly, the cells exposed to Cellax exhibited greater suppression of viability compared to free DTX, when the DTX was supplied in a bolus dose. DTX is an anti-mitotic antineoplastic drug which binds to tubulin and impedes cell replication, ultimately inducing apoptosis and cell death.[90] Cells surviving the initial exposure to DTX can continue to replicate in the absence of subsequent DTX administration. In the metronomic-dose study with the EMT-6 and LL/2 cell lines, wherein the IC50 dose of DTX was applied in four separate doses over two days, the viability of the cell lines was lower, with IC50's comparable to that of Cellax (Table 3). Compared to free DTX, the Cellax polymer releases DTX continuously, and this sustained release model may represent a preferred modality for this class of drug. A number of recent reports have emphasized the benefit of continuous DTX exposure, as opposed to burst release. For example, De Souza reported that DTX release i.p. from a chitosan/laurinaldehyde/egg phosphatidylcholine/DTX gel (DTX-PoLi$_{gel}$) exhibited significant activity against SKOV3-luc xenograft ovarian tumors compared to intermittent treatment with DTX.[91] In preclinical and clinical studies, the administration of lower and more frequent doses of chemotherapeutic (metronomic therapy) has been observed to improve efficacy, with effects being attributed to increased cell death and anti-angiogenesis effects.[92-93] Other workers with DTX and PTX conjugates have noted the enhanced IC50's of their formulations. For example, Esmaeili et al. reported that albumin-DTX was more effective than DTX, and attributed this effect to improved transendothelial transport.[68] In this study, we verified in the EMT-6 mammary and LL/2 lung carcinoma lines a benefit to metronomic therapy in vitro, and interestingly, the IC50 of Cellax and metronomic DTX were equivalent. Current opinion holds that polymer conjugates accumulating in the tumor compartment will not only release more drug locally, but may be steadily internalized by the cells (either by pinocytosis or specific receptor mediated interactions), leading to increased release of the drug in the cytoplasm.[1, 47] Certain conjugates (including Xyotax and HPMA entities) appear to bypass the multiple drug resistance (MDR) and p-gp pathways, an advantage over small molecule therapies which often face MDR limitations.[47, 94] At this point in the study the mechanism by which Cellax improves effect has not been elucidated, and represents a focus for ongoing studies.

As established in the in vitro assay, the PEG-cellulose component of the nanoparticle carrier is water soluble and non-toxic to murine mammary EMT-6 and lung LL/2 cell lines. Furthermore, in an MTD study in Balb/c mice, no observable weight loss or toxicity was measured over a 1 week period following 20 and 40 mg/kg DTX equivalents of Cellax, compared to mild toxicity measured in mice treated with 20 and 40 mg/kg free DTX (FIG. 5B). At higher doses of 85 and 170 mg/kg Cellax, minimal toxicity was observed, and a true MTD for Cellax cannot be established in a one-dose test as particle concentration reaches a maximum of 15 mg DTX/mL, or a 50 mg Cellax polymer/mL concentration. No indication of organ toxicity could be detected in Balb/c and C57/BL6 mice at the 40 mg/kg dosing for Cellax (FIG. 8B), but renal and pulmonary toxicity were an issue for DTX therapy. At high doses of 170 mg/kg Cellax, no organ abnormalities were detected by histology and immunohistochemistry analyses (data not shown).

MRI analysis of SPION-loaded Cellax particles was undertaken to measure tumor accumulation, and establish residency estimates for these particles. SPIONS generate local magnetic susceptibility gradients that rapidly diphase nearby transverse magnetization and produce good negative contrast in MRI images.[41, 95] It is known from the preliminary experiment examining SPION in a microplate that the relaxation time of the T2 signal is appreciable (>100 ms) at reasonable concentrations (FIG. 3A). As seen in FIGS. 3B and C, the T2 and T2* intensity of the tumor tissue pre-injection is higher than the neighboring tissues. Post-injection (FIGS. 3D and 3E) the Cellax-SPIONS accumulated in discrete areas, many nearer the surface of the tumor, creating a visible perimeter on the two nodular sections of the tumor. Over the course of three days, the particles remain readily visible, and as the tumor volume continued to expand, the particle distribution became more distributed in volume, but remained concentrated within the original locations. As shown in FIG. 3F, the volume fraction of hypointense (contrast) voxels corresponding to Cellax-SPION peaks at 24 hours, and begins to drop off at 72 hours. As the tumor volume continued to grow over the 72 hour study period, it is not known at this point whether the reduction in hypointense volume fraction was due to elimination of the SPIONs or only due to increase in tumor volume.

The one-dose treatment of EMT-6 tumors with Cellax produced a notable reduction in tumor growth (FIG. 7A) compared to controls (p<0.001) and DTX alone (p<0.05). Compared to non-covalently taxane loaded micelles, the Cellax conjugate performed well. For example, Garrec et al loaded polyvinylpyrrolidone-polylactic acid copolymer micelles with PTX and dosed with 60 mg/kg on day 0, 1, 2, 7, 8 and 9, and achieved marginal non-significant reductions in tumor volume by day 14. The authors noted that the rapid clearance of PTX from the micelles and were aware of the rapid partitioning of PTX from the micelles.[96] Conjugating the taxane to a polymer appears to substantially enhance PK and efficacy. For example, Li reported on polyglumex (Xyotax) and indicated the improved PK[85] and an excellent response against ovarian (OCA-1) tumors in mice with cure at 160 mg/kg.[97] At 80 mg/kg, the PTX-polyglumex improved efficacy compared to PTX, but did not cure the tumors. Xyotax was effective (although less so compared to the OCA-1 study) in reducing tumor growth in SCOV3ip1 and MDA-MB-231 xenograft models, and in syngeneic hepatocellular and sarcoma models.[98] The pilot Cellax efficacy study was conducted at dose-matching concentrations of DTX and Cellax (40 mg/kg), and Cellax demonstrated a significant advantage over DTX alone. The histology analysis of the EMT-6 tumors indicted that DTX and Cellax induce apoptosis (FIG. 8A, TUNEL staining), with Cellax inducing significantly more apoptosis compared to DTX (p<0.001) or controls (p<0.0001), somewhat contrary to apoptosis analysis in the polyglumex study by Li,[97] where the apoptosis index was in fact less for polyglumex. The same pattern of tissue necrosis is seen in both Li's study and with Cellax-treated tumors, and furthermore, the CD31 (angiogenesis) and Ki67 (cell replication) indexes for the Cellax treated tumors are substantially lower compared to controls (p<0.0001) and DTX treated tumors (p<0.05 and p<0.01 respectively). The one-dose treatment of LL/2 tumors with Cellax likewise significantly reduced the tumor growth compared to controls and DTX-treated tumors (FIG. 7B), although not to the same extent as seen with the EMT-6 model. Interestingly, the DTX-treated LL/2 tumors showed almost no sign of apoptosis (FIG. 9B) and tumor growth was not limited compared to controls (FIG. 7B). We extended our analysis of the EMT-6 mammary cell line in a metastatic study, to determine if this particularly aggressive form of tumor could be effectively treated with Cellax. By histology analysis, i.v. injected EMT-6 cells accumulated principally in the lungs (FIG. 11C), with visibly reduced tumor volume for the Cellax treated mice (40 mg/kg). As seen in FIGS. 11A and 11B, weight loss was reduced and mouse survival was significantly extended with Cellax treatment, and as importantly, visible signs of pain or distress including piloerection, hind leg paresis, seizure, and apathy were not detected in Cellax treated mice, but these symptoms were in evidence for control and DTX-treated mice, necessitating their sacrifice. As control mice likewise exhibited these symptoms, it is unlikely the physical issues were related to DTX-induced neuropathy (a serious dose-limiting side effect for docetaxel),[99] but rather, due to the extended effects of the metastatic cancer.[100] Docetaxel is in clinical trials for therapy against pancreatic cancer that has metastasized to the i.p. space, and accordingly, this study also examined the effect of Cellax against this form of cancer. Mice inoculated with PAN02 cells (and not treated) exhibited signs of disease five days post-inoculation (FIG. 12), and experienced rapid decline. Treatment with 120 mg/kg gemcitabine did not confer significantly increased benefits to the mice. Conversely, mice treated with DTX and Cellax (40 mg/kg) did not present with symptoms for longer periods, and survival was significantly extended.

In summary, we have reported in this example the synthesis of a carboxymethylcellulose-based macromolecule containing a hydrophobic drug, docetaxel, and a PEG unit, a structure designed to assemble into well defined nanoparticles in aqueous solutions. Cellulose is a well known and biocompatible material with an extensive safety profile. The methods for preparing Cellax particles were optimized to yield 100 nm scale particles with a cmc of 0.1 mg/mL, 37 wt % DTX content, and 5 wt % PEG. The Cellax particles increase the MTD for docetaxel in mice models to >170 mg/kg compared to 40 mg/kg for free DTX, and are more effective that DTX against murine breast and lung cancer lines in vivo. A one-dose treatment of 40 mg/kg Cellax effectively minimized the growth of murine EMT-6 and LL/2 flank tumors: immunohistochemical and histology analysis indicating increased apoptosis in Cellax treated tumors, and reduced microvessel formation and cell replication. Furthermore, Cellax was particularly effective against a metastatic breast cancer model in Balb/c mice, and further studies will investigate the mechanism by which Cellax doubled survival time and reduced clinical symptoms of bone metastases and chord compression.

Example 3

Camptothecin, Doxorubicin (DOX) and Paclitaxel Particles

The synthesis of Camptothecin-PEG-CMC illustrates that very hydrophobic drugs can be successfully conjugated to CMC-Ac, enabling the delivery of otherwise insoluble drug. A different synthetic and purification scheme was used than for DTX, tailored to this compound's specific chemistry and solubility.

Conjugation of DOX to the CMC-Ac was synthetically successful, but the materials do not possess self-assembling properties required for nanoparticle formation, underscoring the requirement of a hydrophobic drug in the design of this drug delivery system.

Paclitaxel and docetaxel are both commonly used anticancer drugs, and preparation of PTX and DTX analogues had equivalent synthetic and purification processes.

Example 4

PEG5000 Analogue of Cellax

It is preferred to use PEG with a MW=2000, as extraction of excess PEG by trituration is straightforward. However, higher MW PEG conjugates may enhance the PK of certain nanoparticles, and accordingly a PEG5000 analogue was synthesized: the material demonstrates the desired self-assembly properties.

Example 5

Lower MW CMC Analogue

CMC is available in a range of MW's, but are characterized principally by viscosity and degree of substitution due to difficulties in analyzing MW, as would be understood by a person skilled in the art. A variant produced with CMC (MW 20000) produced a particle of 140 nm.

Example 6

TEM Analysis of the Cellax Particle

TEM analysis of the Cellax was performed. The particle sizing data from the Zetasizer and TEM measurements are similar (100-120 nm).

Example 7

Incorporation of CMT into a Cellax Particle

Incorporation of hydrophobic entities such as CMT (and SPIONs) has been demonstrated: particle size is stable and similar to Cellax particles, and high incorporation efficiency is observed. The non-covalent incorporation of drug or imaging agents provide for multifunctional particles containing more than one drug or imaging functionality.

Although preferred embodiments of the invention have been described herein, it will be understood by those skilled in the art that variations may be made thereto without departing from the spirit of the invention or the scope of the appended claims. All references mentioned herein, including in the following list of references, are incorporated by reference in their entirety.

REFERENCE LIST

1. Li C, Wallace S. Polymer-drug conjugates: recent development in clinical oncology. Adv Drug Deliv Rev. 2008 May 22; 60(8):886-98.
2. Duncan R. The dawning era of polymer therapeutics. Nat Rev Drug Discov. 2003 May; 2(5):347-60.
3. Ringsdorf H. Structure and properties of pharmacologically active polymers. Journal of Polymer Science, Polymer Symposia. 1975; 51:135-53.
4. Yamaoka T, Tabata Y, Ikada Y. Distribution and tissue uptake of poly(ethylene glycol) with different molecular weights after intravenous administration to mice. J Pharm Sci. 1994 April; 83(4):601-6.
5. Seymour L W, Duncan R, Strohalm J, Kopecek J. Effect of molecular weight (Mw) of N-(2-hydroxypropyl)methacrylamide copolymers on body distribution and rate of excretion after subcutaneous, intraperitoneal, and intravenous administration to rats. J Biomed Mater Res. 1987 November; 21(11):1341-58.
6. Duncan R. Development of HPMA copolymer-anticancer conjugates: clinical experience and lessons learnt. Adv Drug Deliv Rev. 2009 Nov. 12; 61(13):1131-48.
7. Matsumura Y, Maeda H. A new concept for macromolecular therapeutics in cancer chemotherapy: mechanisms of tumoritropic accumulation of proteins and the antitumor agent smancs. Cancer Research. 1986; 46:6387-92.
8. Hashizume H, Baluk P, Morikawa S, McLean J W, Thurston G, Roberge S, et al. Openings between defective endothelial cells explain tumor vessel leakiness. Am J Pathol. 2000 April; 156(4): 1363-80.
9. Hobbs S K, Monsky W L, Yuan F, Roberts W G, Griffith L, Torchilin V P, et al. Regulation of transport pathways in tumor vessels: role of tumor type and microenvironment. Proc Natl Acad Sci USA. 1998 Apr. 14; 95(8):4607-12.
10. Greish K. Enhanced permeability and retention (EPR) effect for anticancer nanomedicine drug targeting. Methods Mol Biol. 2010; 624:25-37.
11. Greish K. Enhanced permeability and retention of macromolecular drugs in solid tumors: a royal gate for targeted anticancer nanomedicines. J Drug Target. 2007 August-September; 15(7-8):457-64.
12. Yuan F, Dellian M, Fukumura D, Leunig M, Berk D A, Torchilin V P, et al. Vascular permeability in a human tumor xenograft: molecular size dependence and cutoff size. Cancer Res. 1995 Sep. 1; 55(17):3752-6.
13. Gabizon A, Shmeeda H, Barenholz Y. Pharmacokinetics of pegylated liposomal Doxorubicin: review of animal and human studies. Clin Pharmacokinet. 2003; 42(5):419-36.
14. Drummond D C, Noble C O, Hayes M E, Park J W, Kirpotin D B. Pharmacokinetics and in vivo drug release rates in liposomal nanocarrier development. J Pharm Sci. 2008 November; 97(11):4696-740.
15. Lindner L H, Hossann M. Factors affecting drug release from liposomes. Curr Opin Drug Discov Devel. 2010 January; 13(1):111-23.
16. Hamaguchi T, Kato K, Yasui H, Morizane C, Ikeda M, Ueno H, et al. A phase I and pharmacokinetic study of NK105, a paclitaxel-incorporating micellar nanoparticle formulation. Br J Cancer. 2007 Jul. 16; 97(2):170-6.
17. Hamaguchi T, Matsumura Y, Suzuki M, Shimizu K, Goda R, Nakamura I, et al. NK105, a paclitaxel-incorporating micellar nanoparticle formulation, can extend in vivo antitumour activity and reduce the neurotoxicity of paclitaxel. Br J Cancer. 2005 Apr. 11; 92(7):1240-6.
18. Lavasanifar A, Samuel J, Kwon G S. Poly(ethylene oxide)-block-poly(L-amino acid) micelles for drug delivery. Adv Drug Deliv Rev. 2002 Feb. 21; 54(2):169-90.
19. Ahmed F, Pakunlu R I, Brannan A, Bates F, Minko T, Discher D E. Biodegradable polymersomes loaded with both paclitaxel and doxorubicin permeate and shrink tumors, inducing apoptosis in proportion to accumulated drug. J Control Release. 2006 Nov. 28; 116(2):150-8.
20. Discher D E, Ahmed F. Polymersomes. Annu Rev Biomed Eng. 2006; 8:323-41.
21. Katz J S, Levine D H, Davis K P, Bates F S, Hammer D A, Burdick J A. Membrane stabilization of biodegradable polymersomes. Langmuir. 2009 Apr. 21; 25(8):4429-34.
22. Svenson S, Tomalia D A. Dendrimers in biomedical applications—reflections on the field. Adv Drug Deliv Rev. 2005 Dec. 14; 57(15):2106-29.
23. Tekade R K, Kumar P V, Jain N K. Dendrimers in oncology: an expanding horizon. Chem Rev. 2009 January; 109(1):49-87.
24. Tomalia D A, Reyna L A, Svenson S. Dendrimers as multi-purpose nanodevices for oncology drug delivery and diagnostic imaging. Biochem Soc Trans. 2007 February; 35(Pt 1):61-7.
25. Misra R, Acharya S, Sahoo S K. Cancer nanotechnology: application of nanotechnology in cancer therapy. Drug Discov Today. 2010 October; 15(19-20):842-50.
26. Gaucher G, Marchessault R H, Leroux J C. Polyester-based micelles and nanoparticles for the parenteral delivery of taxanes. J Control Release. 2010 Apr. 2; 143(1):2-12.
27. Li S D, Huang L. Pharmacokinetics and biodistribution of nanoparticles. Mol Pharm. 2008 July-August; 5(4):496-504.
28. Harris J M, Zalipsky S, American Chemical Society. Division of Polymer Chemistry., American Chemical Society. Meeting. Poly(ethylene glycol): chemistry and biological applications. Washington, D.C.: American Chemical Society; 1997.
29. Immordino M L, Dosio F, Cattel L. Stealth liposomes: review of the basic science, rationale, and clinical applications, existing and potential. Int J Nanomedicine. 2006; 1(3):297-315.
30. Owens D E, 3rd, Peppas N A. Opsonization, biodistribution, and pharmacokinetics of polymeric nanoparticles. Int J Pharm. 2006 Jan. 3; 307(1):93-102.
31. Harris J M, Martin N E, Modi M. Pegylation: a novel process for modifying pharmacokinetics. Clin Pharmacokinet. 2001; 40(7):539-51.
32. Wang X, Li J, Wang Y, Cho K J, Kim G, Gjyrezi A, et al. HFT-T, a targeting nanoparticle, enhances specific delivery of paclitaxel to folate receptor-positive tumors. ACS Nano. 2009 Oct. 27; 3(10):3165-74.
33. Dubey P K, Mishra V, Jain S, Mahor S, Vyas S P. Liposomes modified with cyclic RGD peptide for tumor targeting. J Drug Target. 2004 June; 12(5):257-64.
34. Shishido T, Mieda H, Hwang S Y, Nishimura Y, Tanaka T, Ogino C, et al. Affibody-displaying bionanocapsules for specific drug delivery to HER2-expressing cancer cells. Bioorg Med Chem Lett. 2010 Oct. 1; 20(19):5726-31.
35. Kirpotin D B, Drummond D C, Shao Y, Shalaby M R, Hong K, Nielsen U B, et al. Antibody targeting of long-circulating lipidic nanoparticles does not increase tumor localization but does increase internalization in animal models. Cancer Res. 2006 Jul. 1; 66(13):6732-40.
36. Harding F A, Stickler M M, Razo J, Dubridge R B. The immunogenicity of humanized and fully human antibodies: residual immunogenicity resides in the CDR regions. MAbs. 2010 May; 2(3):256-65.
37. Koning G A, Kamps J A, Scherphof G L. Interference of macrophages with immunotargeting of liposomes. J Liposome Res. 2002 February-May; 12(1-2):107-19.
38. Andresen T L, Jensen S S, Jorgensen K. Advanced strategies in liposomal cancer therapy: problems and prospects of active and tumor specific drug release. Prog Lipid Res. 2005 January; 44(1):68-97.
39. Landais P, Meresse V, Ghislain J C. Evaluation and validation of diagnostic tests for guiding therapeutic decisions. Therapie. 2009 May-June; 64(3):187-201.
40. de Smet M, Heijman E, Langereis S, Hijnen N, Grull H. Magnetic resonance imaging of high intensity focused ultrasound mediated drug delivery from temperature sensitive liposomes; An in vivo proof-of-concept study. J Control Release. 2010 Nov. 5.

41. Branca R T, Cleveland Z I, Fubara B, Kumar C S, Maronpot R R, Leuschner C, et al. Molecular MRI for sensitive and specific detection of lung metastases. Proc Natl Acad Sci USA. 2010 Feb. 23; 107(8):3693-7.
42. Kaida S, Cabral H, Kumagai M, Kishimura A, Terada Y, Sekino M, et al. Visible drug delivery by supramolecular nanocarriers directing to single-platformed diagnosis and therapy of pancreatic tumor model. Cancer Res. 2010 Sep. 15; 70(18):7031-41.
43. Hoang B, Lee H, Reilly R, Allen C. Non-Invasive Monitoring of the Fate of 111In-Labeled Block Copolymer Micelles by High Resolution and High Sensitivity MicroSPECT/CT Imaging. Mol Pharm. 2009 Feb. 2.
44. Saravanakumar G, Min K H, Min D S, Kim A Y, Lee C M, Cho Y W, et al. Hydrotropic oligomer-conjugated glycol chitosan as a carrier of paclitaxel: synthesis, characterization, and in vivo biodistribution. J Control Release. 2009 Dec. 16; 140(3):210-7.
45. Lim W T, Tan E H, Toh C K, Hee S W, Leong S S, Ang P C, et al. Phase I pharmacokinetic study of a weekly liposomal paclitaxel formulation (Genexol-PM) in patients with solid tumors. Ann Oncol. 2010 February; 21(2):382-8.
46. Letchford K, Liggins R, Wasan K M, Burt H. In vitro human plasma distribution of nanoparticulate paclitaxel is dependent on the physicochemical properties of poly(ethylene glycol)-block-poly(caprolactone) nanoparticles. Eur J Pharm Biopharm. 2009 February; 71(2):196-206.
47. Duncan R. Polymer conjugates as anticancer nanomedicines. Nat Rev Cancer. 2006 September; 6(9):688-701.
48. Morais J M, Papadimitrakopoulos F, Burgess D J. Biomaterials/tissue interactions: possible solutions to overcome foreign body response. AAPS J. 2010 June; 12(2):188-96.
49. Ertel S I, Ratner B D, Kaul A, Schway M B, Horbett T A. In vitro study of the intrinsic toxicity of synthetic surfaces to cells. J Biomed Mater Res. 1994 June; 28(6):667-75.
50. Santerre J P, Woodhouse K, Laroche G, Labow R S. Understanding the biodegradation of polyurethanes: from classical implants to tissue engineering materials. Biomaterials. 2005 December; 26(35):7457-70.
51. FDA. Inactive Ingredients Database. Rockville; 2010.
52. Liu Z, Jiao Y, Wang Y, Zhou C, Zhang Z. Polysaccharides-based nanoparticles as drug delivery systems. Adv Drug Deliv Rev. 2008 Dec. 14; 60(15):1650-62.
53. Janes K A, Calvo P, Alonso M J. Polysaccharide colloidal particles as delivery systems for macromolecules. Adv Drug Deliv Rev. 2001 Mar. 23; 47(1):83-97.
54. Prabaharan M. Review paper: chitosan derivatives as promising materials for controlled drug delivery. J Biomater Appl. 2008 July; 23(1):5-36.
55. Prabaharan M, Mano J F. Chitosan-based particles as controlled drug delivery systems. Drug Deliv. 2005 January-February; 12(1):41-57.
56. Cera C, Palumbo M, Stefanelli S, Rassu M, Palu G. Water-soluble polysaccharide-anthracycline conjugates: biological activity. Anticancer Drug Des. 1992 April; 7(2):143-51.
57. Uglea C V, Pary A, Corjan M, Dumitriu A D, Ottenbrite R M. Biodistribution and antitumor activity induced by carboxymethylcellulose conjugates. Journal of Bioactive and Compatible Polymers. 2005; 20:571-83.
58. Auzenne E, Ghosh S C, Khodadadian M, Rivera B, Farquhar D, Price R E, et al. Hyaluronic acid-paclitaxel: antitumor efficacy against CD44(+) human ovarian carcinoma xenografts. Neoplasia. 2007 June; 9(6):479-86.
59. Inoue K, Kumazawa E, Kuga H, Susaki H, Masubuchi N, Kajimura T. CM-dextran-polyalcohol-camptothecin conjugate: DE-310 with a novel carrier system and its preclinical data. Adv Exp Med Biol. 2003; 519:145-53.
60. Soepenberg O, de Jonge M J, Sparreboom A, de Bruin P, Eskens F A, de Heus G, et al. Phase I and pharmacokinetic study of DE-310 in patients with advanced solid tumors. Clin Cancer Res. 2005 Jan. 15; 11(2 Pt 1):703-11.
61. Lipinski C A. Drug-like properties and the causes of poor solubility and poor permeability. J Pharmacol Toxicol Methods. 2000 July-August; 44(1):235-49.
62. Singla A K, Garg A, Aggarwal D. Paclitaxel and its formulations. Int J Pharm. 2002 Mar. 20; 235(1-2):179-92.
63. Shelley W B, Talanin N, Shelley E D. Polysorbate 80 hypersensitivity. Lancet. 1995 May 20; 345(8960):1312-3.
64. Gelderblom H, Verweij J, Nooter K, Sparreboom A. Cremophor E L: the drawbacks and advantages of vehicle selection for drug formulation. Eur J Cancer. 2001 September; 37(13):1590-8.
65. Jones S. Head-to-head: Docetaxel challenges paclitaxel. EJC Supplements. 2006; 4:4-8.
66. Etrych T, Sirova M, Starovoytova L, Rihova B, Ulbrich K. HPMA copolymer conjugates of paclitaxel and docetaxel with pH-controlled drug release. Mol Pharm. 2010 Aug. 2; 7(4):1015-26.
67. Liu J, Zahedi P, Zeng F, Allen C. Nano-sized assemblies of a PEG-docetaxel conjugate as a formulation strategy for docetaxel. J Pharm Sci. 2008 August; 97(8):3274-90.
68. Esmaeili F, Dinarvand R, Ghahremani M H, Amini M, Rouhani H, Sepehri N, et al. Docetaxel-albumin conjugates: preparation, in vitro evaluation and biodistribution studies. J Pharm Sci. 2009 August; 98(8):2718-30.
69. Hou W, Watters J W, McLeod H L. Simple and rapid docetaxel assay in plasma by protein precipitation and high-performance liquid chromatography-tandem mass spectrometry. J Chromatogr B Analyt Technol Biomed Life Sci. 2004 May 25; 804(2):263-7.
70. Kumar D, Tomar R S, Deolia S K, Mitra M, Mukherjee R, Burman A C. Isolation and characterization of degradation impurities in docetaxel drug substance and its formulation. J Pharm Biomed Anal. 2007 Mar. 12; 43(4):1228-35.
71. Kerns E H, Volk K J, Hill S E, Lee M S. Profiling taxanes in Taxus extracts using lc/ms and lc/ms/ms techniques. J Nat Prod. 1994 October; 57(10):1391-403.
72. Namikoshi H, inventor Daicel Chemical Industries Ltd, assignee. Carboxyalkyl acetyl celluloses, their salts and a process for the preparation of them. USA. 1985.
73. Sun S, Zeng H. Size-controlled synthesis of magnetite nanoparticles. J Am Chem Soc. 2002 Jul. 17; 124(28):8204-5.
74. Zhang X, Jackson J K, Burt H M. Determination of surfactant critical micelle concentration by a novel fluorescence depolarization technique. J Biochem Biophys Methods. 1996 Feb. 5; 31(3-4):145-50.
75. Wijsman J H, Jonker R R, Keijzer R, van de Velde C J, Cornelisse C J, van Dierendonck J H. A new method to detect apoptosis in paraffin sections: in situ end-labeling of fragmented DNA. J Histochem Cytochem. 1993 January; 41(1):7-12.
76. FDA. Home>Medical Devices>Products and Medical Procedures>Device Approvals and Clearances: OP-1 Putty-H020008. 2010.
77. FDA. Database of Select Committee on GRAS Substances (SCOGS) Reviews. 2010.

78. Sugahara S, Kajiki M, Kuriyama H, Kobayashi T R. Complete regression of xenografted human carcinomas by a paclitaxel-carboxymethyl dextran conjugate (AZ10992). J Control Release. 2007 Jan. 22; 117(1):40-50.
79. Charpentier D, Mocanu G, Carpov A, Chapelle S, Merle L, Muller G. New hydrophobically modified carboxymethylcellulose derivitives. Carbohydrate Polymers. 1997; 33:177-86.
80. Facchini A, Segatti F, inventors; LIMA Lto SpA, assignee. N-methyl-amine derivitives of Carboxymethylcellulose, alginic acid N-methyl-amide or carboxymethyl starch. 2005.
81. Allen J M, Wilson A K, Luca P L, Curtis L G, inventors; Process for preparing carboxyalkyl cellulose esters. U.S. Pat. No. 5,792,856. 1998.
82. Fairley N, Hoang B, Allen C. Morphological control of poly(ethylene glycol)-block-poly(epsilon-caprolactone) copolymer aggregates in aqueous solution. Biomacromolecules. 2008 September; 9(9):2283-91.
83. Fanzioni S, Hovda K, Livi V, KcKennon M, Siviero L, Spoonemore H, inventors; Cell Therapeutics, assignee. Method for determining the amount of conjugated taxane in polyglut acid—taxne conjugates. USA. 2010.
84. Kerns E H, Volk K J, Hill S E. Profiling new taxanes using LC/MS and LC/MS/MS substructural analysis techniques. Rapid Communications in Mass Spectrometry. 1995; 9:1539-45.
85. Li C, Newman R A, Wu Q P, Ke S, Chen W, Hutto T, et al. Biodistribution of paclitaxel and poly(L-glutamic acid)-paclitaxel conjugate in mice with ovarian OCa-1 tumor. Cancer Chemother Pharmacol. 2000; 46(5):416-22.
86. Wang X, Zhao G, Van S, Jiang N, Yu L, Vera D, et al. Pharmacokinetics and tissue distribution of PGG-paclitaxel, a novel macromolecular formulation of paclitaxel, in nu/nu mice bearing NCI-460 lung cancer xenografts. Cancer Chemother Pharmacol. 2010 February; 65(3):515-26.
87. Feng Z, Zhao G, Yu L, Gough D, Howell S B. Preclinical efficacy studies of a novel nanoparticle-based formulation of paclitaxel that out-performs Abraxane. Cancer Chemother Pharmacol. 2010 April; 65(5):923-30.
88. Liu B, Yang M, Li R, Ding Y, Qian X, Yu L, et al. The antitumor effect of novel docetaxel-loaded thermosensitive micelles. Eur J Pharm Biopharm. 2008 June; 69(2): 527-34.
89. EU. Assessment Report: Docefrez. In: Agency E M, editor. London; 2010.
90. Yvon A M, Wadsworth P, Jordan M A. Taxol suppresses dynamics of individual microtubules in living human tumor cells. Mol Biol Cell. 1999 April; 10(4):947-59.
91. De Souza R, Zahedi P, Mariyama E, H., Allen C, Wilson B C, Paquette-Miller M. Continuous docetaxel chemotherapy improves therapeutic efficacy in murine models of ovarian cancer. Molecular Cancer Therapeutics. 2010; 9(6):1820-30.
92. Lord R, Nair S, Schache A, Spicer J, Somaihah N, Khoo V, et al. Low dose metronomic oral cyclophosphamide for hormone resistant prostate cancer: a phase II study. J Urol. 2007 June; 177(6): 2136-40; discussion 40.
93. Kamat A A, Kim T J, Landen C N, Jr., Lu C, Han L Y, Lin Y G, et al. Metronomic chemotherapy enhances the efficacy of antivascular therapy in ovarian cancer. Cancer Res. 2007 Jan. 1; 67(1):281-8.
94. Singer J W, Shaffer S, Baker B, Bernareggi A, Stromatt S, Nienstedt D, et al. Paclitaxel poliglumex (XYOTAX; CT-2103): an intracellularly targeted taxane. Anticancer Drugs. 2005 March; 16(3):243-54.
95. Dias M H M, Lauterbur P C. Ferromagnetic particles as contrast agents for magnetic resonance imaging of liver and spleen. Megnetic Resonance in Medicine. 1986; 3:328-30.
96. Le Garrec D, Gori S, Luo L, Lessard D, Smith D C, Yessine M A, et al. Poly(N-vinylpyrrolidone)-block-poly (D,L-lactide) as a new polymeric solubilizer for hydrophobic anticancer drugs: in vitro and in vivo evaluation. J Control Release. 2004 Sep. 14; 99(1):83-101.
97. Li C, Yu D F, Newman R A, Cabral F, Stephens L C, Hunter N, et al. Complete regression of well-established tumors using a novel water-soluble poly(L-glutamic acid)-paclitaxel conjugate. Cancer Res. 1998 Jun. 1; 58(11): 2404-9.
98. Li C, Price J E, Milas L, Hunter N R, Ke S, Yu D F, et al. Antitumor activity of poly(L-glutamic acid)-paclitaxel on syngeneic and xenografted tumors. Clin Cancer Res. 1999 April; 5(4):891-7.
99. Hilkens P H, Verweij J, Vecht C J, Stoter G, van den Bent M J. Clinical characteristics of severe peripheral neuropathy induced by docetaxel (Taxotere). Ann Oncol. 1997 February; 8(2):187-90.
100. Sasaki A, Boyce B F, Story B, Wright K R, Chapman M, Boyce R, et al. Bisphosphonate risedronate reduces metastatic human breast cancer burden in bone in nude mice. Cancer Res. 1995 Aug. 15; 55(16):3551-7.

What is claimed is:

1. A compound comprising an acetylated carboxymethylcellulose (CMC-Ac) covalently linked to: at least one poly (ethylene glycol) (PEG) and at least one hydrophobic drug.
2. The compound of claim 1, wherein the covalent linkages are ester linkages.
3. The compound of claim 1, wherein the at least one hydrophobic drug is an anticancer agent.
4. The compound of claim 3, wherein the at least one hydrophobic drug is one of docetaxel, camptothecin and paclitaxel.
5. The compound of claim 4, wherein the at least one PEG is poly(ethylene glycol) methyl ether (mPEG) having an average $M_n$ of between about 550 and about 10,000.
6. The compound of claim 5, wherein the at least one PEG is poly(ethylene glycol) methyl ether (mPEG) has an average $M_n$ of about 2000.
7. The compound of claim 5, wherein the CMC consists of between about 95 and 3600 monomer units.
8. The compound of claim 7, wherein the CMC consists of about 3500 monomer units.
9. The compound of claim 7, wherein the molar ratio of (CMC-Ac acetyl groups):(CMC-Ac carboxylic acid groups/ PEG/hydrophobic drug) is between about 2.5:0.5-1.8:1.2.
10. The compound of claim 9, wherein the molar ratio of (CMC-Ac acetyl groups):(CMC-Ac carboxylic acid groups/ PEG/hydrophobic drug) is about 2.18:0.82.
11. The compound of claim 9, wherein the mPEG is present in an amount of about 3.5-22.7 weight %, and the docetaxel is present in an amount of about 22.5-43.3 weight %.
12. The compound of claim 11, wherein the mPEG is present in an amount of about 4.7-5.3 weight %, and the docetaxel is present in an amount of about 30.1-39.5 weight %.
13. The compound of claim 12, wherein the mPEG is present in an amount of 4.7 weight %, and the docetaxel is present in an amount of 36.9 weight %.
14. The compound of claim 13, wherein the molar ratio of mPEG:docetaxel:(CMC-Ac carboxylic acid groups) is from about 0.9:13.4:85.7 to about 5.4:26.4:68.2, as estimated by $^1$H NMR analysis.

15. The compound of claim 14, wherein the molar ratio of mPEG:docetaxel:(CMC-Ac carboxylic acid groups) is about 1:15.1:83.6 to 1.1:23.7:75.3.

16. The compound of claim 1, wherein the CMC-Ac is further covalently linked to at least one imaging agent.

17. A self-assembling nanoparticle composition comprising the compound of claim 1.

18. The self-assembling nanoparticle composition of claim 17, wherein the composition has a critical micelle concentration (cmc) of about 0.1 mg/mL.

19. The self-assembling nanoparticle composition of claim 17, wherein the nanoparticles have an average diameter of about 49-278 nm.

20. The compound of claim 15, wherein the molar ratio of mPEG:docetaxel:(CMC-Ac carboxylic acid groups) is about 1:20.1:78.5.

21. The compound of claim 16, wherein the CMC-Ac is further covalently linked Cy5.5.

22. The self-assembling nanoparticle composition of claim 19, wherein the nanoparticles have an average diameter with a range of 16-396 nm.

23. The self-assembling nanoparticle composition of claim 17, further comprising at least one hydrophobic agent encapsulated therein.

24. The self-assembling nanoparticle composition of claim 23, wherein the at least one hydrophobic agent is an imaging agent or a therapeutic agent.

25. The self-assembling nanoparticle composition of claim 23, wherein the at least one imaging agent is a superparamagnetic iron oxide nanoparticle (SPION).

26. The self-assembling nanoparticle composition of claim 25, wherein the at least one imaging agent is between 7-30 weight % SPION, and more preferably about 30 weight % SPION.

27. The self-assembling nanoparticle composition of claim 25, wherein the at least one imaging agent is about 30 weight % SPION.

28. A pharmaceutical composition comprising the self-assembling nanoparticle composition of claim 17 and a pharmaceutically acceptable carrier and/or diluent.

29. The compound of claim 1 represented by the formula:

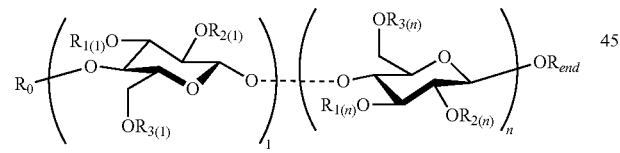

wherein $R_0$, $R_{1(1)} \ldots R_{1(n)}$, $R_{2(1)} \ldots R_{2(n)}$, $R_{3(1)} \ldots R_{3(n)}$, and $R_{end}$ are each independently selected from:

(a) acetyl;

(b)

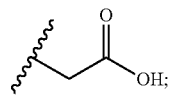

(c)

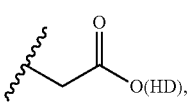

wherein —O(HD) represents a hydrophobic drug having a point of attachment via a hydroxyl group; or (d)

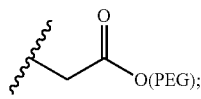

and n is an integer >94.

30. The compound of claim 29, wherein the ratio of (a):(b+c+d) is about 2.18:0.82.

31. The compound of claim 30, wherein n is between about 95 and 3600 monomer units.

32. The compound of claim 31, wherein the hydrophobic drug is one of docetaxel, camptothecin and paclitaxel.

33. The compound of claim 32, wherein the PEG is mPEG.

34. The compound of claim 29, wherein n is about 3500.

35. A method for providing sustained-release delivery of a hydrophobic drug to a patient in need thereof comprising administering to the patient an effective amount of the self-assembling nanoparticle composition as defined in claim 17.

36. A process for preparing a self-assembling nanoparticle composition comprising:
  a) covalently linking at least one PEG and at least one hydrophobic drug to a CMC-Ac;
  b) isolating the product of step (a);
  c) dissolving the isolated product of step (b) in a suitable organic solvent, preferably DMF or DMSO and further preferably THF or acetonitrile, to form a solution;
  d) adding the solution of step (c) dropwise to an aqueous solution under conditions suitable for forming the self-assembling nanoparticle composition.

* * * * *